(12) United States Patent
Muthusamy et al.

(10) Patent No.: US 10,993,943 B2
(45) Date of Patent: May 4, 2021

(54) CRYSTALLINE FORMS OF SELINEXOR AND PROCESS FOR THEIR PREPARATION

(71) Applicant: WATSON LABORATORIES INC., Corona, CA (US)

(72) Inventors: Anantha Rajmohan Muthusamy, Sivakasi (IN); Sundara Lakshmi Kanniah, Vellore (IN); Akash Ravi, Kochukulam Pathanamthitta (IN); Tonmoy Chitta Das, Kolkata (IN); Rajendra Popat Chemate, Ahmednagar (IN); Anil Kumar Singh, Dombivali (IN); Yogesh Dhananjay Wagh, Thane (IN)

(73) Assignee: WATSON LABORATORIES INC., Corona, CA (US)

( * ) Notice: Subject to any disclaimer, the term of this patent is extended or adjusted under 35 U.S.C. 154(b) by 0 days.

(21) Appl. No.: 16/475,197

(22) PCT Filed: Jan. 5, 2018

(86) PCT No.: PCT/US2018/012450
§ 371 (c)(1),
(2) Date: Jul. 1, 2019

(87) PCT Pub. No.: WO2018/129227
PCT Pub. Date: Jul. 12, 2018

(65) Prior Publication Data
US 2019/0336499 A1 Nov. 7, 2019

(30) Foreign Application Priority Data

Jan. 5, 2017 (IN) .............................. 201711000570
Feb. 16, 2017 (IN) .............................. 201711005484
Mar. 15, 2017 (IN) .............................. 201711008908
May 10, 2017 (IN) .............................. 201711016396

(51) Int. Cl.
*A61K 31/497* (2006.01)

(52) U.S. Cl.
CPC ........ *A61K 31/497* (2013.01); *C07B 2200/13* (2013.01)

(58) Field of Classification Search
CPC .................................................... A61K 31/497
USPC ................................................... 514/255.05
See application file for complete search history.

(56) References Cited

U.S. PATENT DOCUMENTS 8,999,996 B2 * 4/2015 Sandanayaka ..... A61K 31/4196
514/255.06

FOREIGN PATENT DOCUMENTS

WO 2016025904 A1 2/2016
WO WO-2016025904 A1 * 2/2016 ........... A61K 31/497
WO 2017118940 A1 7/2017

OTHER PUBLICATIONS

International Search Report for International Application No. PCT/US2018/012450, International Filing Date Jan. 5, 2018, dated Mar. 15, 2018, 5 pages.
Written Opinion for International Application No. PCT/US2018/012450, International Filing Date Jan. 5, 2018, dated Mar. 15, 2018, 5 pages.

* cited by examiner

*Primary Examiner* — Kahsay Habte
(74) *Attorney, Agent, or Firm* — Cantor Colburn LLP

(57) ABSTRACT

The present disclosure relates to solid state forms of Selinexor, processes for preparation thereof and pharmaceutical compositions thereof.

20 Claims, 20 Drawing Sheets

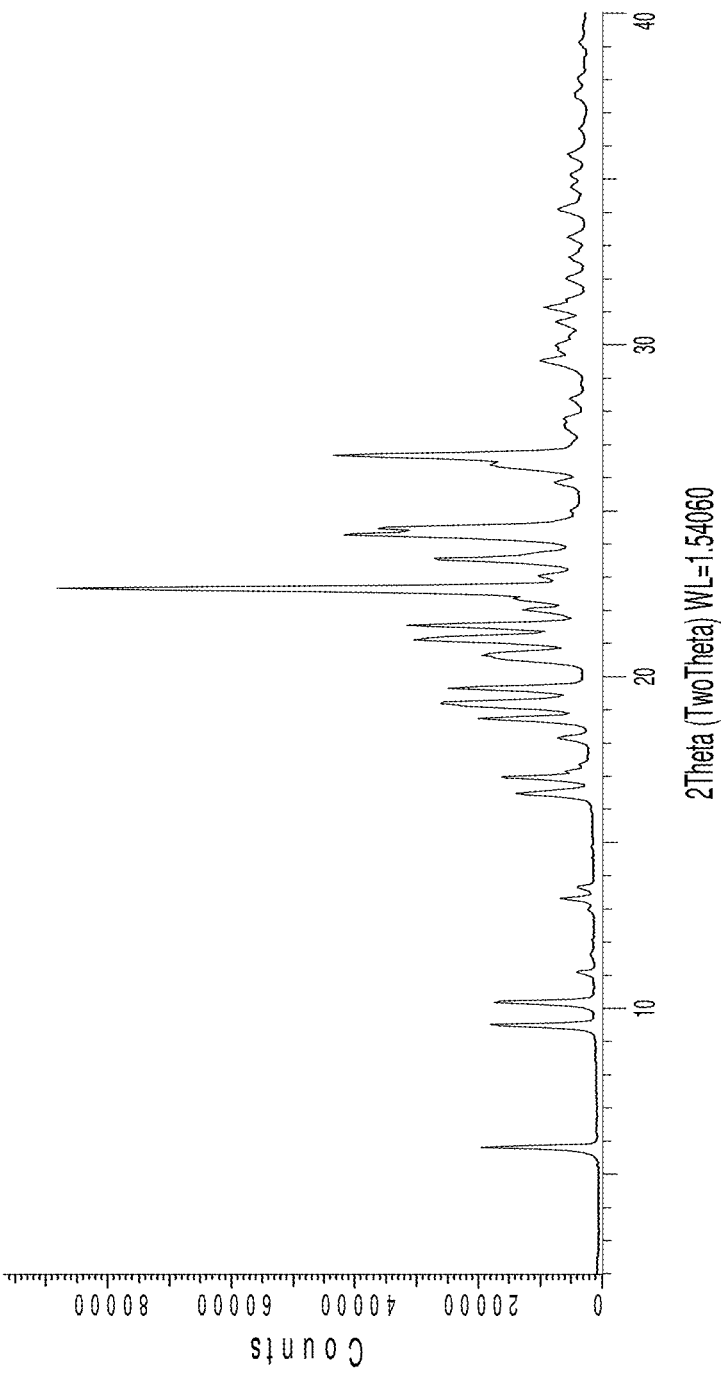
Figure 1. XRPD of form T1 of Selinexor

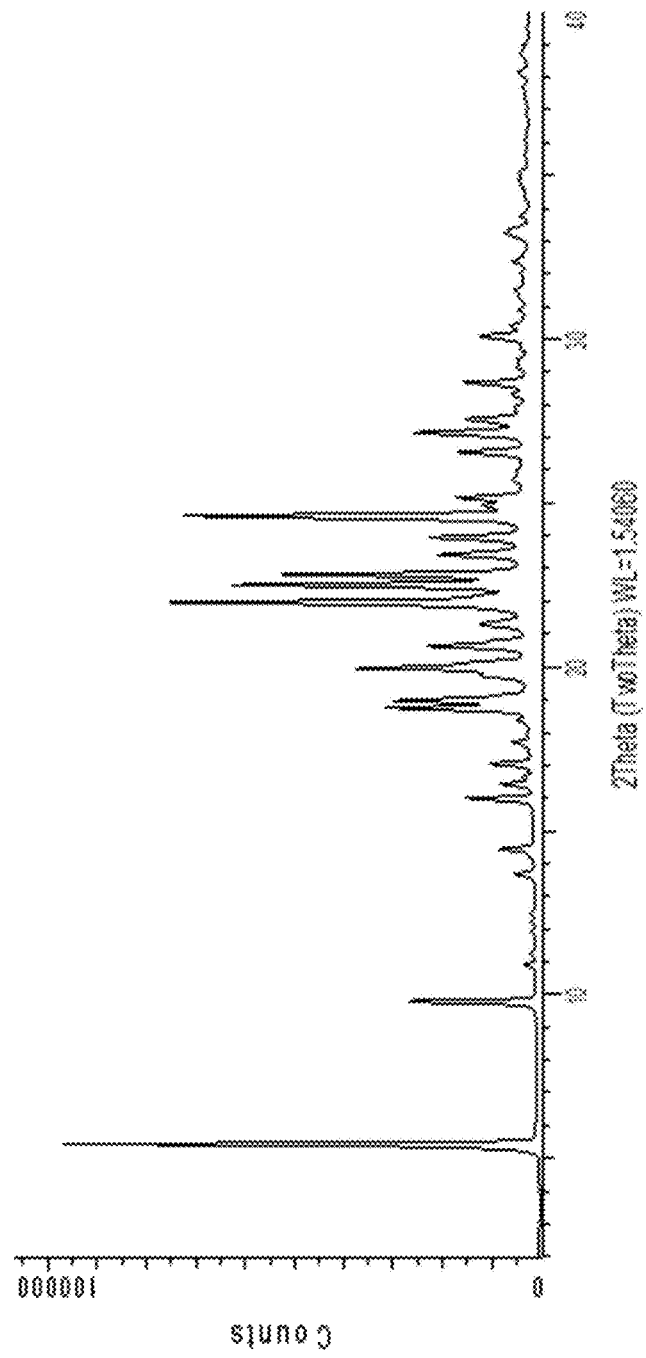
Figure 2. XRPD of form T2 of Selinexor

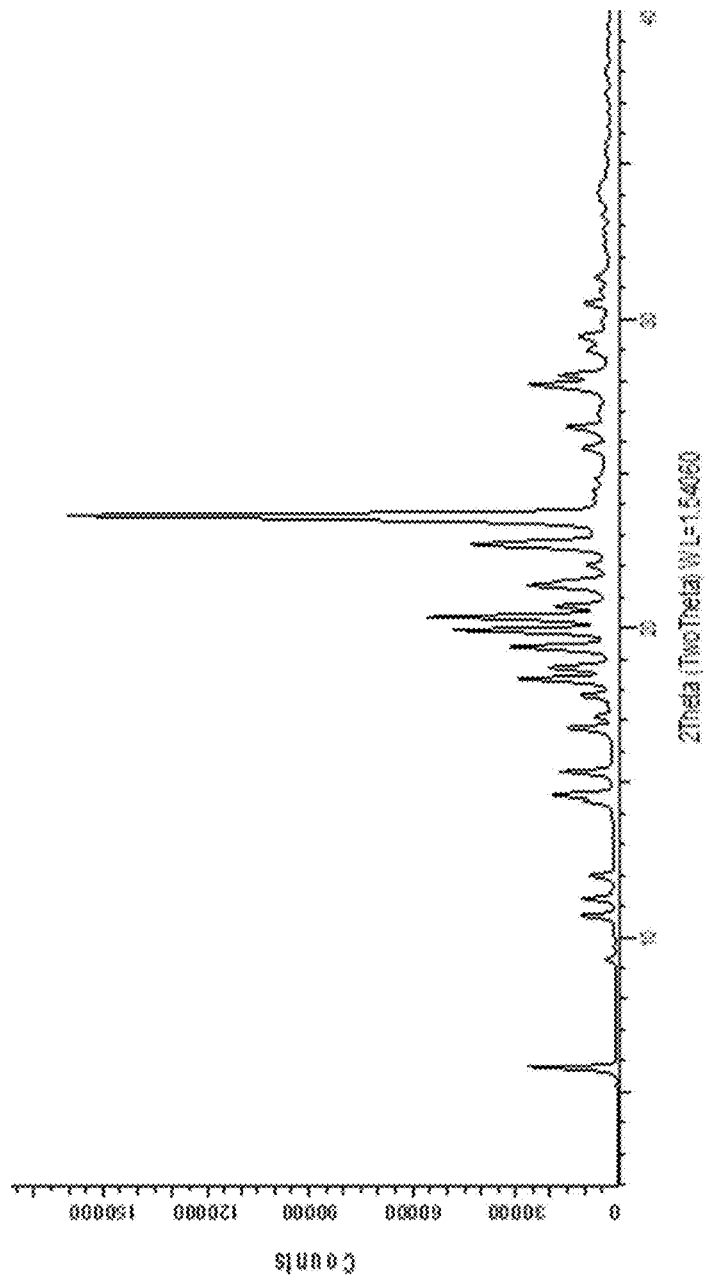
Figure 3. XRPD of form T3 of Selinexor

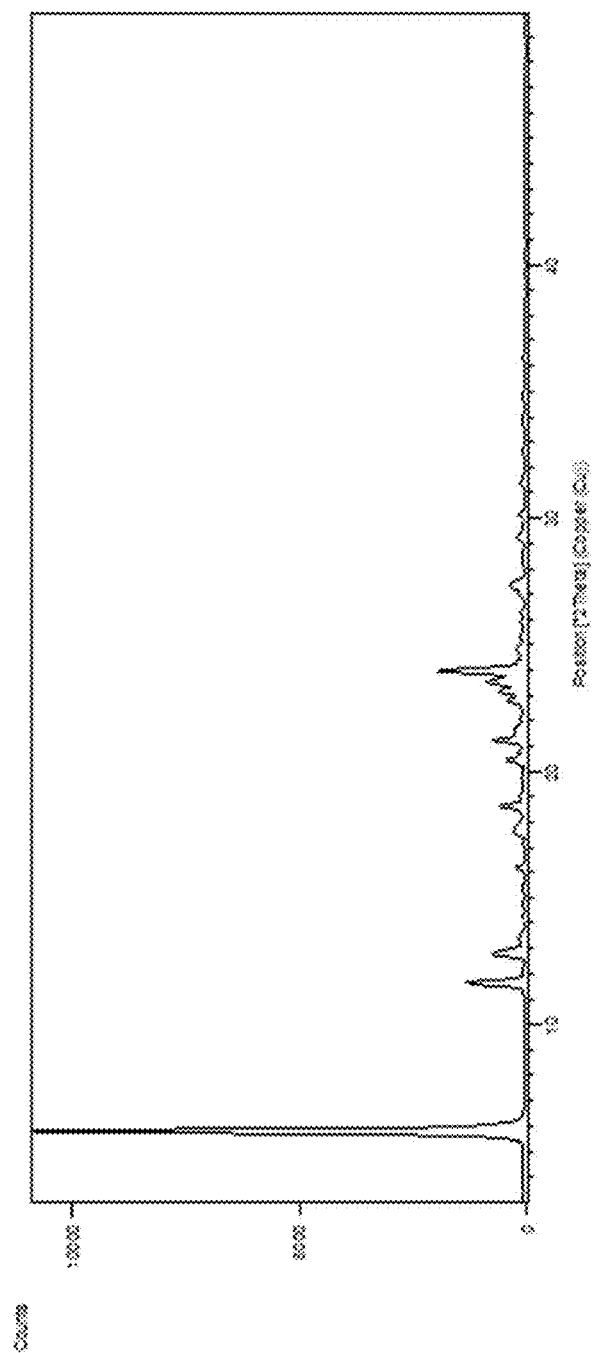
Figure 4. XRPD of form T4 of Selinexor

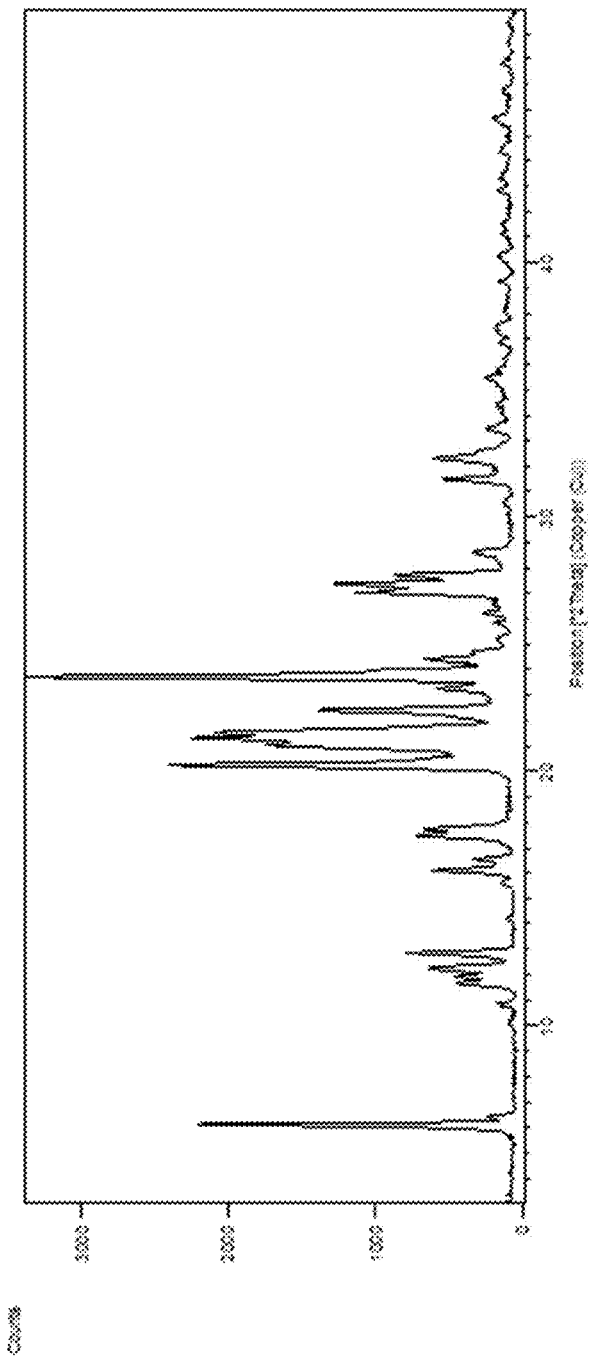
Figure 5. XRPD of form T5 of Selinexor

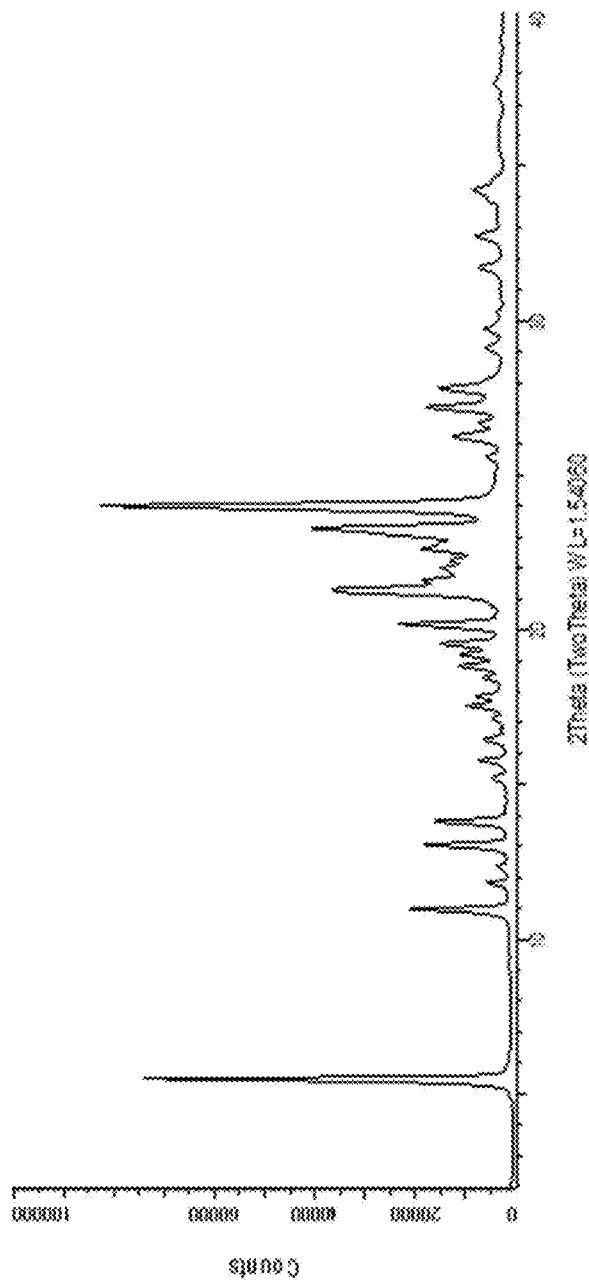
Figure 6. XRPD of form T6 of Selinexor

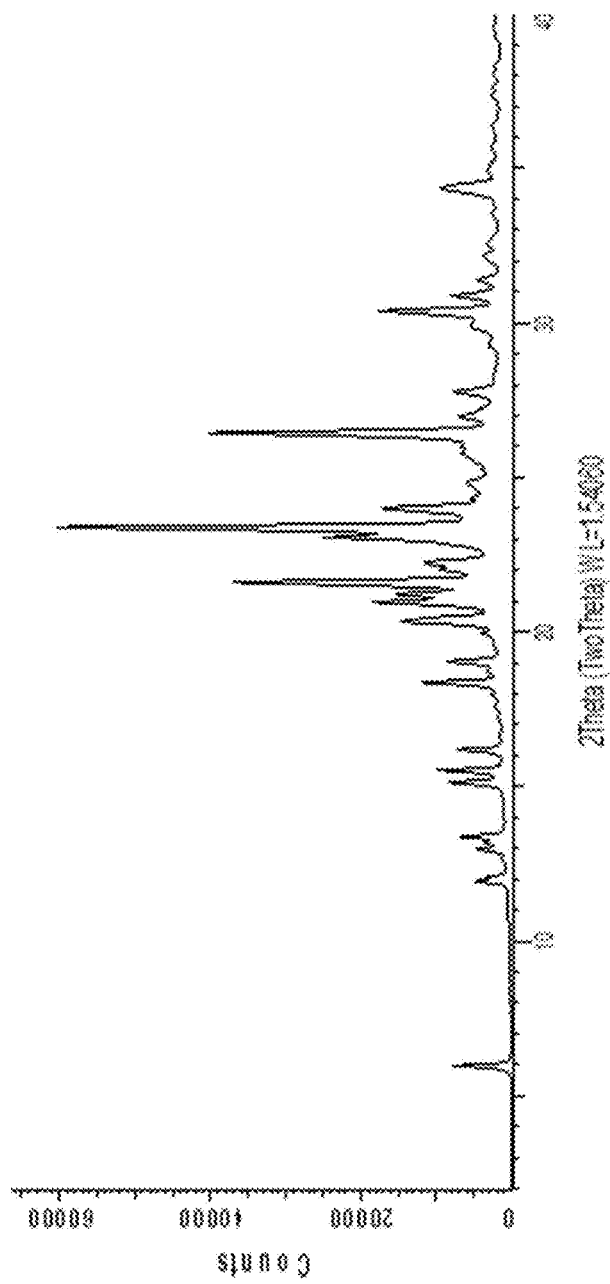
Figure 7. XRPD of form T7 of Selinexor

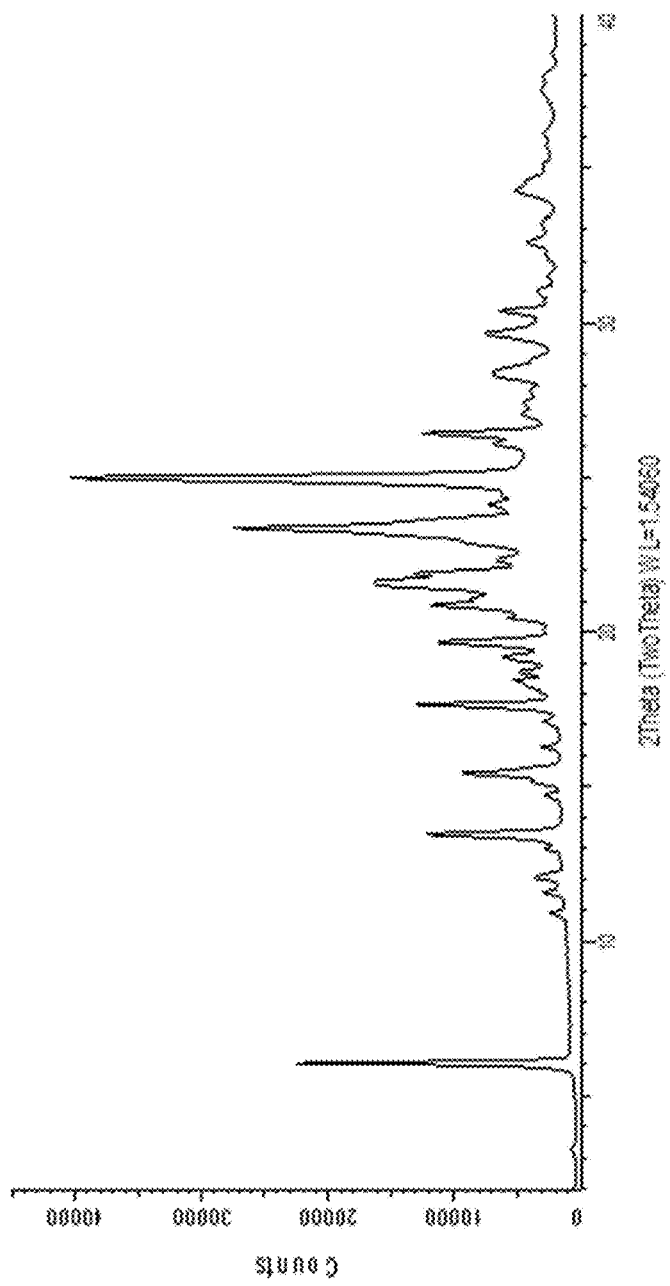
Figure 8. XRPD of form T8 of Selinexor

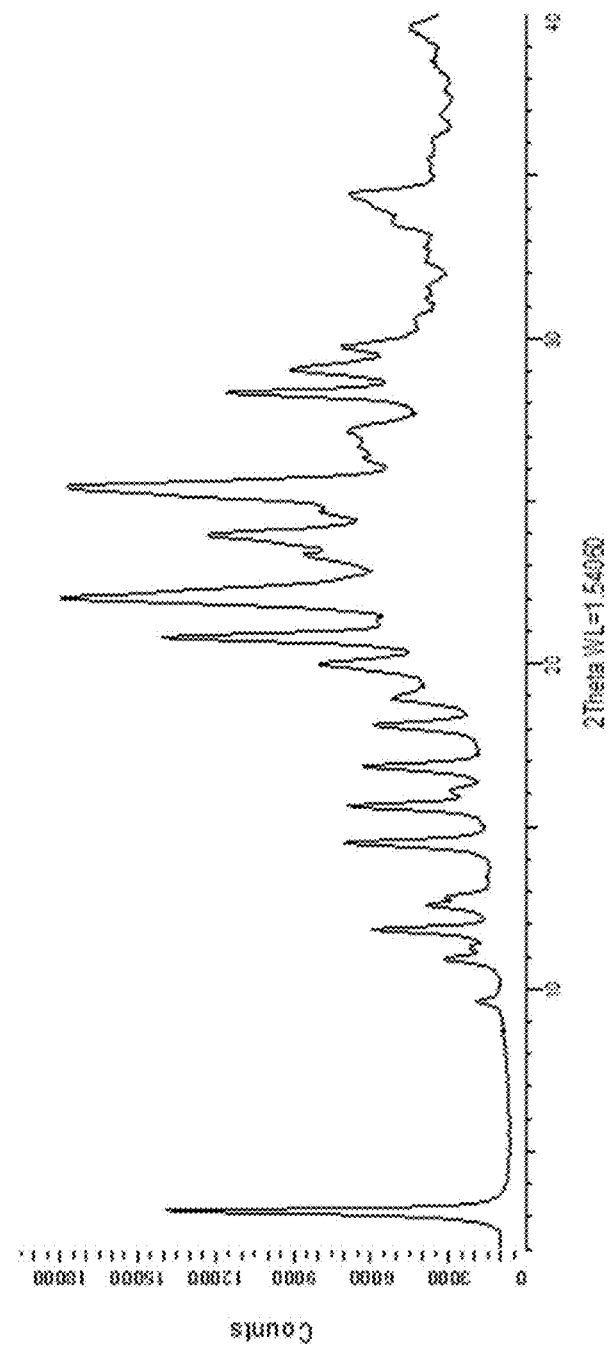
Figure 9. XRPD of form T9 of Selinexor

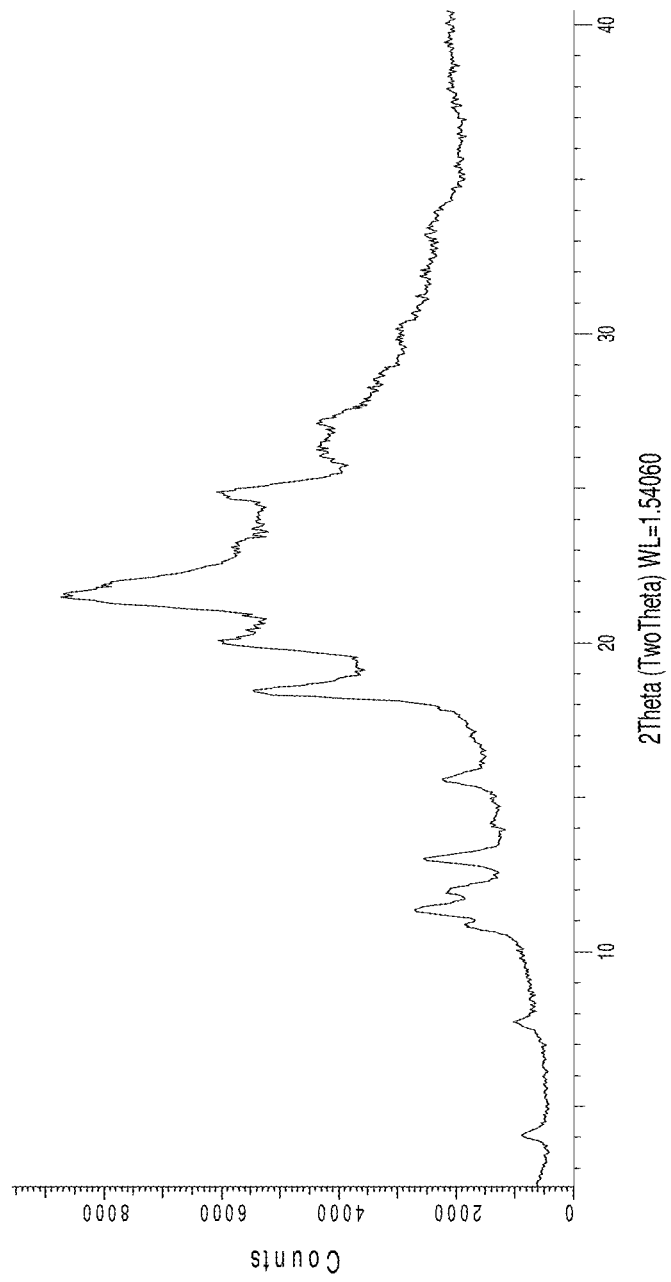
Figure 10. XRPD of form T10 of Selinexor

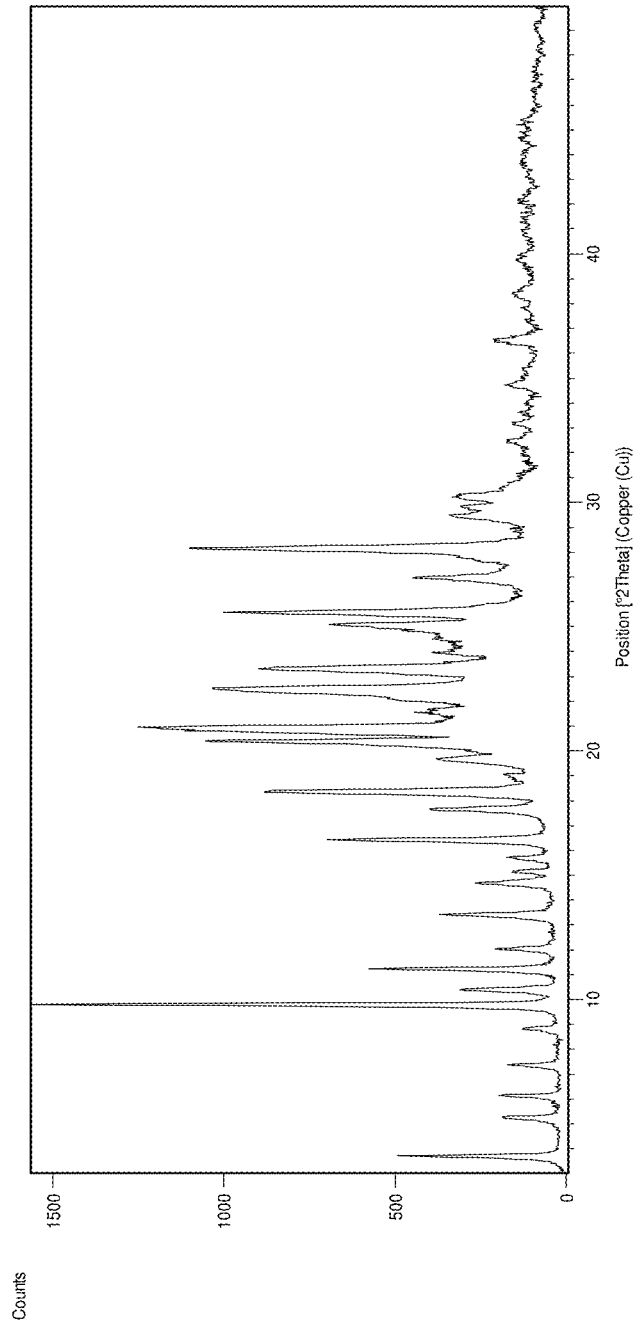
Figure 11. XRPD of form T11 of Selinexor

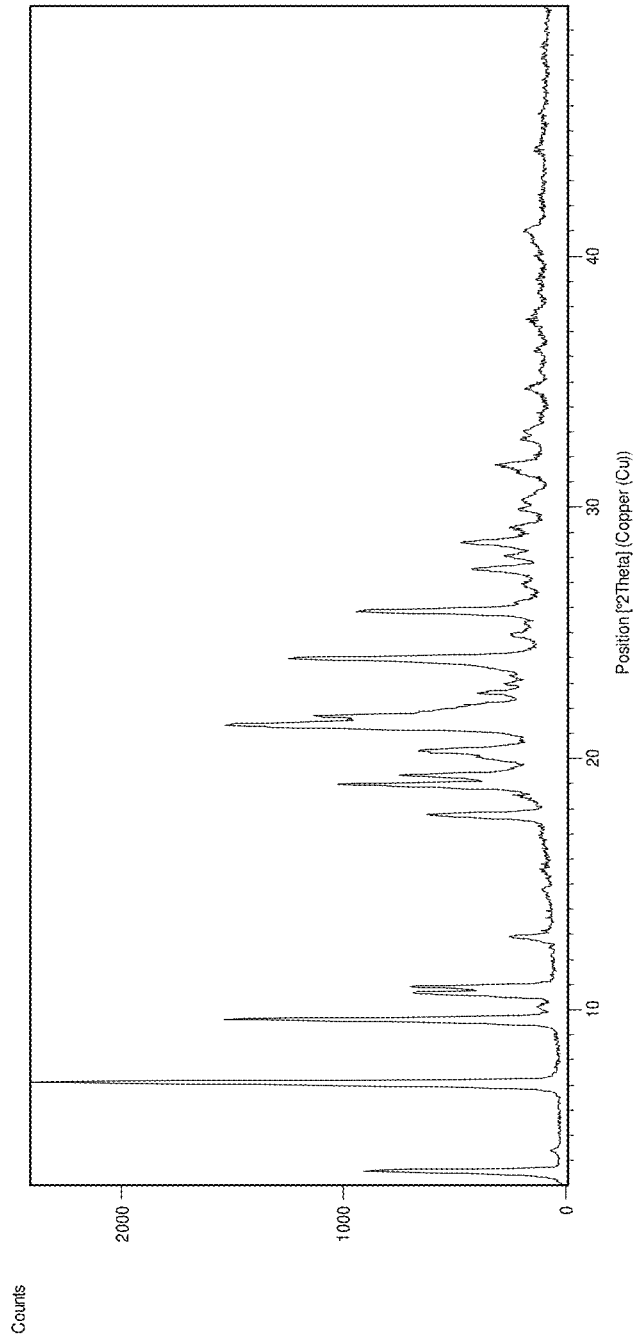
Figure 12. XRPD of form T12 of Selinexor

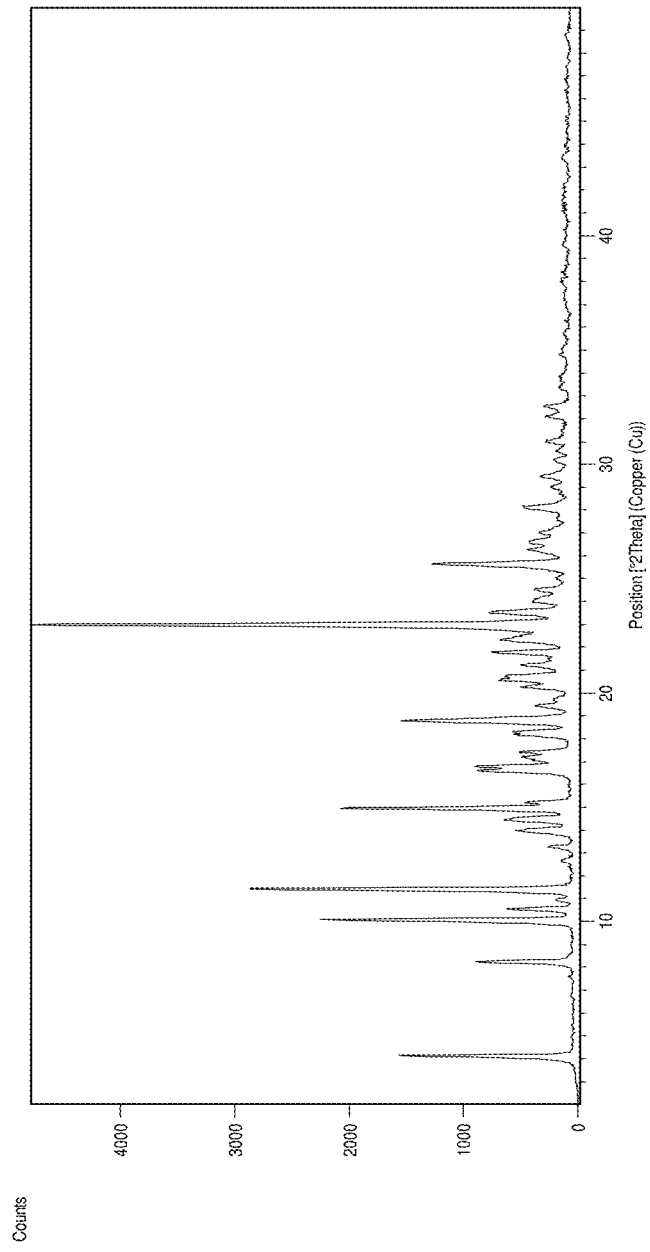
Figure 13. XRPD of form T13 of Selinexor

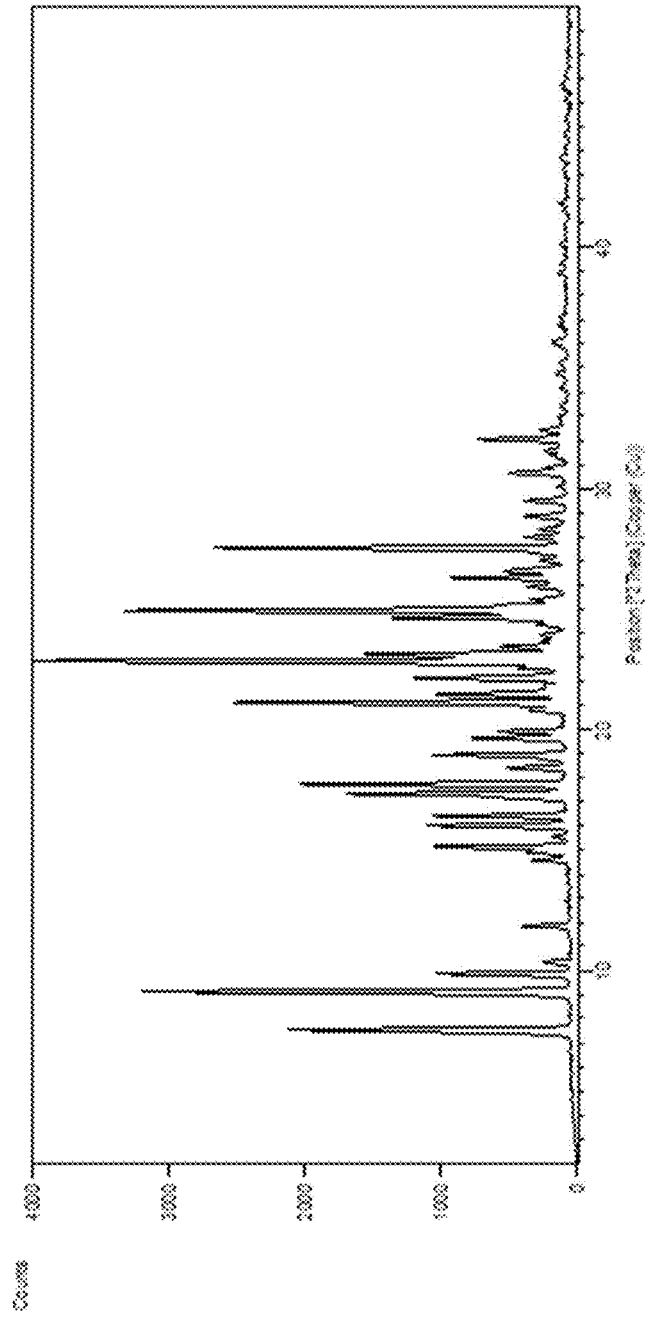
Figure 14. XRPD of form T14 of Selinexor

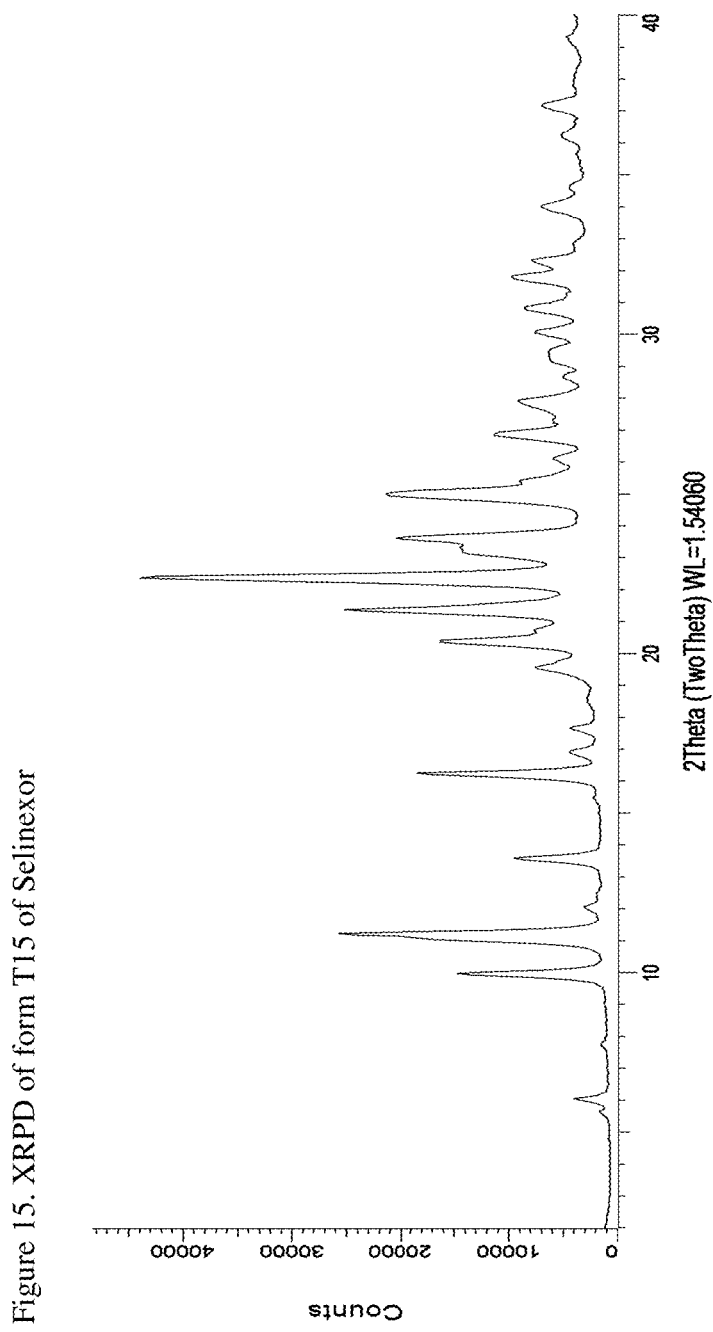
Figure 15. XRPD of form T15 of Selinexor

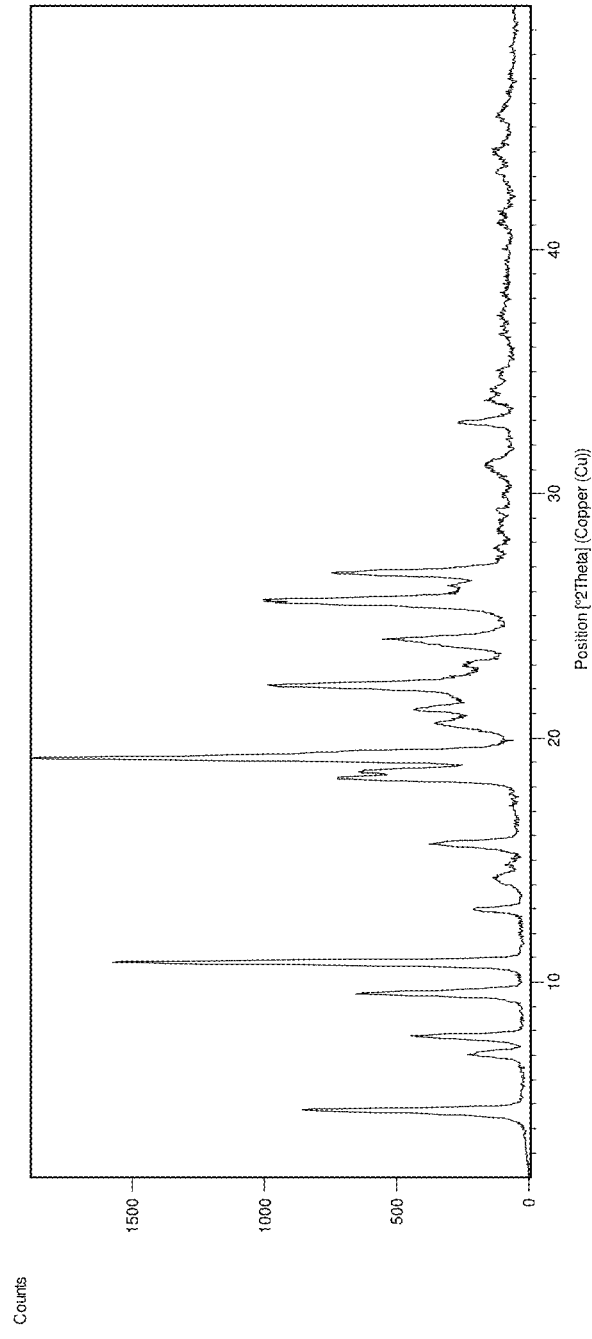
Figure 16. XRPD of form T16 of Selinexor

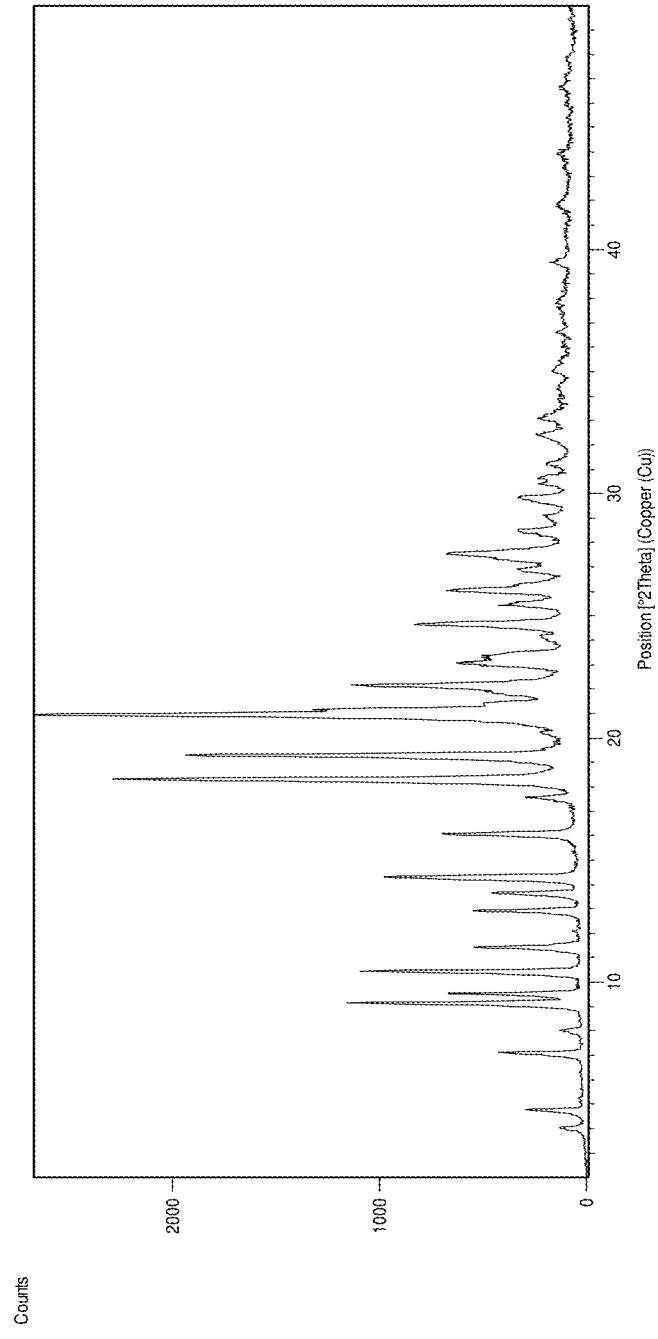
Figure 17. XRPD of form T17 of Selinexor

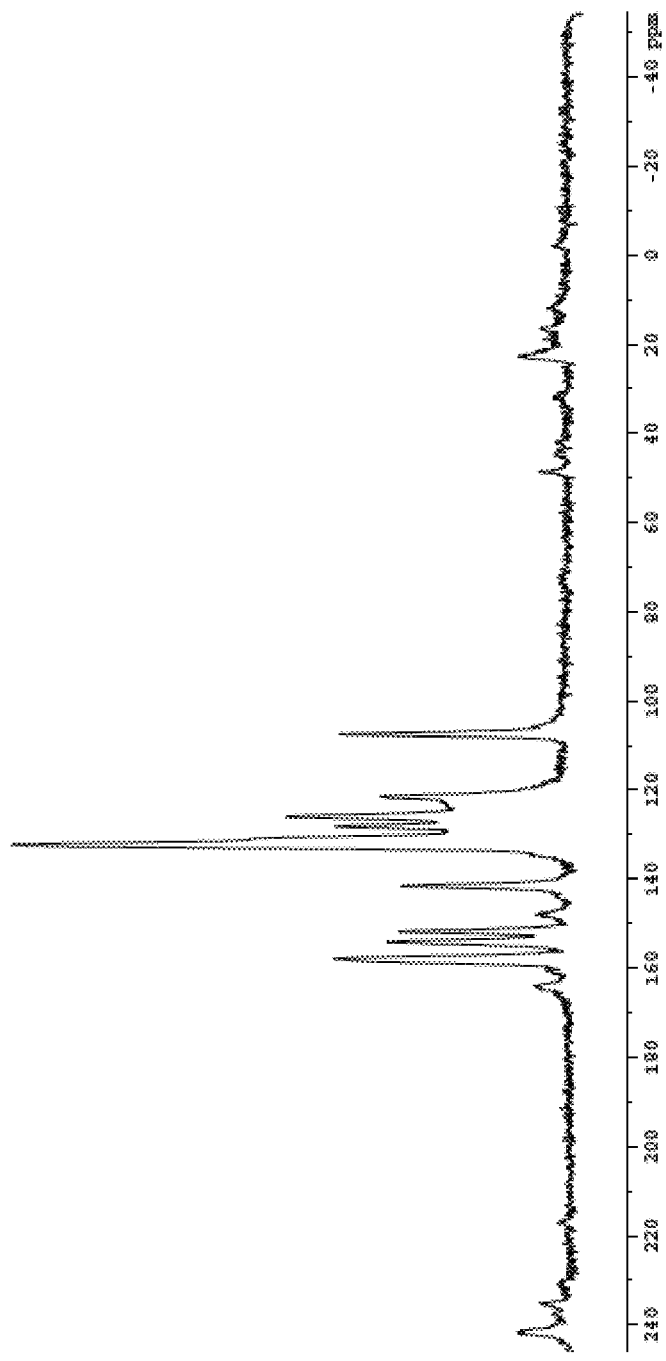
Figure 18. Solid state $^{13}C$ NMR spectrum of form T8 of Selinexor at the range of 200-0 ppm.

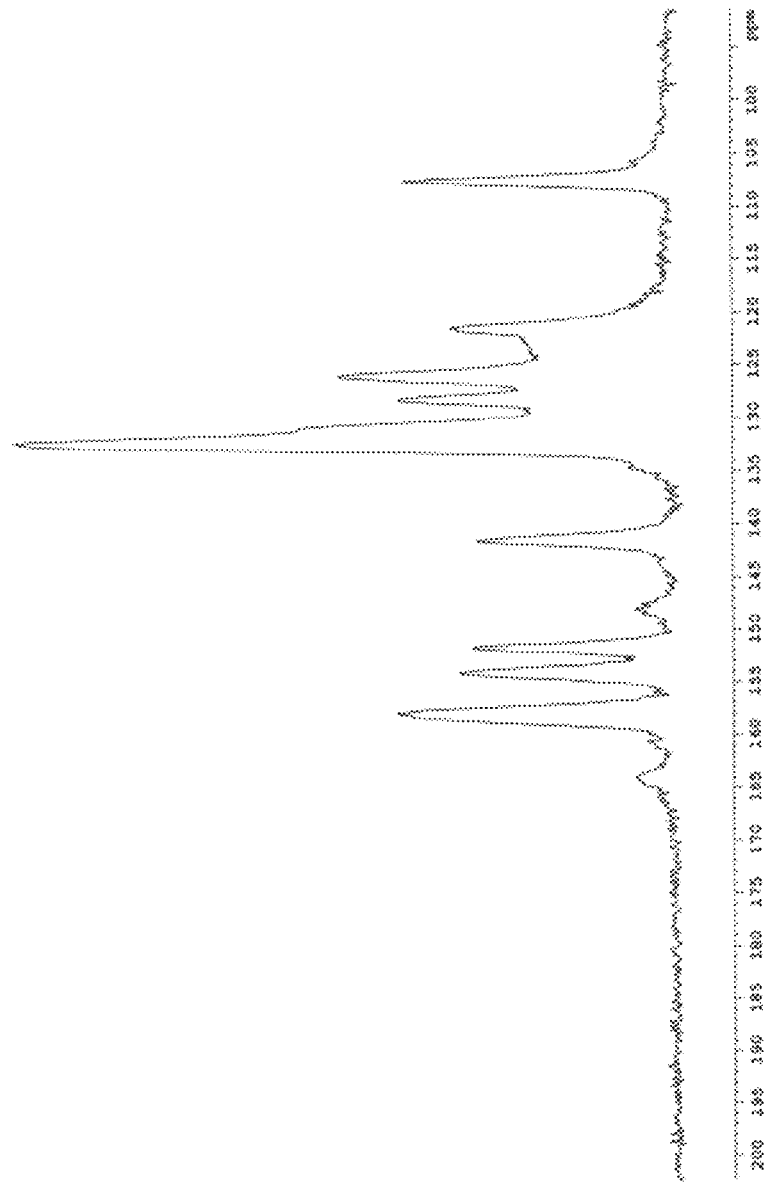
Figure 19. Solid state 13C NMR spectrum of form T8 of Selinexor at the range of 200-100 ppm.

Figure 20. Solid state 13C NMR spectrum of form T8 of Selinexor at the range of 100-0 ppm

CRYSTALLINE FORMS OF SELINEXOR AND PROCESS FOR THEIR PREPARATION

CROSS-REFERENCE TO RELATED APPLICATIONS

This application is a National Stage application of PCT/US2018/012450, filed Jan. 5, 2018, and is related to, and claims the benefit of priority of, IN Application No. 201711016396 filed May 10, 2017, IN Application No. 201711008908 filed on Mar. 15, 2017, IN Application No. 201711005484 filed on Feb. 16, 2017, and IN Application No. 201711000570 filed on Jan. 5, 2017, the contents of each are incorporated herein by reference in their entirety for all purposes.

FIELD OF THE INVENTION

The present disclosure relates to solid state forms of Selinexor, processes for preparation thereof and pharmaceutical compositions thereof.

BACKGROUND OF THE INVENTION

Selinexor has the chemical name (Z)-3-(3-(3,5-bis(trifluoromethyl)phenyl)-1H-1,2,4-triazol-1-yl)-N'-(pyrazin-2-yl) acrylohydrazide. Selinexor has the following chemical structure:

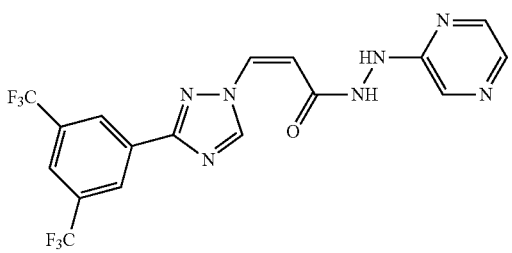 [SMILES: O=C(/C=C\n1cnc(-c2cc(C(F)(F)F)cc(C(F)(F)F)c2)n1)NNc1cnccn1]

Selinexor is a first-in-class selective inhibitor of nuclear export (SINE™) that is being developed by Karyopharm Therapeutics for the treatment of cancer.

Selinexor is known from U.S. Pat. No. 8,999,996 (US'996) and its synthesis is described in Example 2. Selinexor and its crystalline forms: form A, form B, form C and form D as well as their preparation are described in international patent application WO2016025904.

Polymorphism, the occurrence of different crystal forms, is a property of some molecules and molecular complexes. A single compound, like Selinexor, may give rise to a variety of polymorphs having distinct crystal structures and physical properties like melting point, thermal behaviors (e.g. measured by thermogravimetric analysis—"TGA", or differential scanning calorimetry—"DSC"), X-ray powder diffraction (XRPD) pattern, infrared absorption fingerprint (IR/FTIR), Raman absorption fingerprint, and solid state ($^{13}C$—) NMR spectrum. One or more of these techniques may be used to distinguish different polymorphic forms of a compound.

Different solid state forms (including solvated or hydrated forms) of an active pharmaceutical ingredient may possess different properties. Such variations in the properties of different solid state forms and solvates/hydrates may provide a basis for improving formulation, for example, by facilitating better processing or handling characteristics, improving the dissolution profile, or improving stability (polymorphic as well as chemical stability) and shelf-life. These variations in the properties of different solid state forms may also provide improvements to the final dosage form, for instance, if they serve to improve bioavailability. Different solid state forms and solvates/hydrates of an active pharmaceutical ingredient may also give rise to a variety of polymorphs or crystalline forms, which may in turn provide additional opportunities to use variations in the properties and characteristics of a solid active pharmaceutical ingredient for providing an improved product.

Discovering new solid state forms and solvates/hydrates of a pharmaceutical product can provide materials having desirable processing properties, such as ease of handling, ease of processing, storage stability, and ease of purification or as desirable intermediate crystal forms that facilitate conversion to other polymorphic forms. New polymorphic forms and solvates/hydrates of a pharmaceutically useful compound can also provide an opportunity to improve the performance characteristics of a pharmaceutical product (dissolution profile, bioavailability, etc.). It enlarges the repertoire of materials that a formulation scientist has available for formulation optimization, for example by providing a product with different properties, e.g., a different crystal habit, higher crystallinity or polymorphic stability which may offer better processing or handling characteristics, improved dissolution profile, or improved shelf-life. For at least these reasons, there is a need for additional solid state forms (including solvated or hydrated forms) of Selinexor.

SUMMARY OF THE INVENTION

The present disclosure relates to solid state forms of Selinexor, processes for preparation thereof, and pharmaceutical compositions comprising these solid state forms.

In particular the present disclosure provides crystalline forms of Selinexor designated as Forms T1-T17 (defined herein). The present disclosure also provides the uses of any one or a combination of the above described solid state forms of Selinexor for preparing other solid state forms of Selinexor.

The present disclosure further provides processes for preparing Selinexor solid state forms thereof.

The present disclosure further provides synthesis process for preparing Selinexor and intermediates thereof.

The present disclosure further provides purification procedures for the preparation of Selinexor.

In another embodiment, the present disclosure encompasses any one of the above described solid state forms of Selinexor and/or combinations thereof for use in the preparation of pharmaceutical compositions and/or formulations, optionally for the treatment of cancer.

In another embodiment, the present disclosure encompasses uses of any one of the above described solid state forms of Selinexor and/or combinations thereof for the preparation of pharmaceutical compositions and/or formulations.

The present disclosure further provides pharmaceutical compositions comprising any one of, or a mixture of, the solid state forms of Selinexor according to the present disclosure.

In yet another embodiment, the present disclosure encompasses pharmaceutical formulations comprising any one of the above described solid state forms of Selinexor and/or combinations thereof and at least one pharmaceutically acceptable excipient.

The present disclosure encompasses processes to prepare said pharmaceutical formulations of Selinexor comprising combining any one of the above described solid state forms and/or combinations thereof and at least one pharmaceutically acceptable excipient.

Any of the solid state forms defined herein and/or combinations thereof as well as the pharmaceutical compositions or formulations of the solid state forms of Selinexor can be used as medicaments, particularly for the treatment of cancer.

The present disclosure also provides methods of treating cancer; comprising administering a therapeutically effective amount of any one of the solid state forms of Selinexor of the present disclosure and/or combinations thereof, or at least one of the above pharmaceutical compositions or formulations, to a subject suffering from cancer, or otherwise in need of the treatment.

The present disclosure also provides uses of any one of the solid state forms of Selinexor of the present disclosure and/or combinations thereof, or at least one of the above pharmaceutical compositions or formulations for the manufacture of medicaments for treating cancer.

BRIEF DESCRIPTION OF THE FIGURES

FIG. 1 shows an X-ray powder diffractogram (XRPD) of form T1 of Selinexor
FIG. 2 shows an XRPD of form T2 of Selinexor.
FIG. 3 shows an XRPD of form T3 of Selinexor.
FIG. 4 shows an XRPD of form T4 of Selinexor.
FIG. 5 shows an XRPD of form T5 of Selinexor.
FIG. 6 shows an XRPD of form T6 of Selinexor.
FIG. 7 shows an XRPD of form T7 of Selinexor.
FIG. 8 shows an XRPD of form T8 of Selinexor.
FIG. 9 shows an XRPD of form T9 of Selinexor.
FIG. 10 shows XRPD of form T10 of Selinexor.
FIG. 11 shows XRPD of form T11 of Selinexor.
FIG. 12 shows XRPD of form T12 of Selinexor.
FIG. 13 shows XRPD of form T13 of Selinexor.
FIG. 14 shows XRPD of form T14 of Selinexor.
FIG. 15 shows XRPD of form T15 of Selinexor.
FIG. 16 shows XRPD of form T16 of Selinexor.
FIG. 17 shows XRPD of form T17 of Selinexor.
FIG. 18 shows solid state $^{13}$C NMR spectrum of form T8 of Selinexor at the range of 200-0 ppm.
FIG. 19 shows solid state 13C NMR spectrum of form T8 of Selinexor at the range of 200-100 ppm.
FIG. 20 shows solid state 13C NMR spectrum of form T8 of Selinexor at the range of 100-0 ppm.

DETAILED DESCRIPTION OF THE INVENTION

The present disclosure relates to solid state forms of Selinexor, processes for preparation thereof and pharmaceutical compositions comprising at least one of, or a combination of, these solid state forms. The disclosure also relates to the conversion of Selinexor and its solid state forms to other solid state forms of Selinexor.

The Selinexor and solid state forms thereof according to the present disclosure may have advantageous properties selected from at least one of: chemical or polymorphic purity, followability, solubility, dissolution rate, bioavailability, morphology or crystal habit, stability—such as chemical stability as well as thermal and mechanical stability with respect to polymorphic conversion, stability towards dehydration and/or storage stability, a lower degree of hygroscopicity, low content of residual solvents and advantageous processing and handling characteristics such as compressibility, or bulk density.

A crystal form may be referred to herein as being characterized by graphical data "as depicted in" a Figure. Such data include, for example, powder X-ray diffractograms (XRPD) and solid state NMR spectra. As is well-known in the art, the graphical data potentially provides additional technical information to further define the respective solid state form (a so-called "fingerprint") which can not necessarily be described by reference to numerical values or peak positions alone. In any event, the skilled person will understand that such graphical representations of data may be subject to small variations, e.g., in peak relative intensities and peak positions due to factors such as variations in instrument response and variations in sample concentration and purity, which are well known to the skilled person. Nonetheless, the skilled person would readily be capable of comparing the graphical data in the Figures herein with graphical data generated for an unknown crystal form and confirm whether the two sets of graphical data are characterizing the same crystal form or two different crystal forms. A crystal form of Selinexor referred to herein as being characterized by graphical data "as depicted in" a Figure will thus be understood to include any crystal forms of the Selinexor, characterized with the graphical data having such small variations, as are well known to the skilled person, in comparison with the Figure.

A solid state form (or polymorph) may be referred to herein as polymorphically pure or as substantially free of any other solid state (or polymorphic) forms. As used herein in this context, the expression "substantially free of any other forms" will be understood to mean that the solid state form contains about 20% or less, about 10% or less, about 5% or less, about 2% or less, about 1% or less, about 0.5% or less, of any other forms of the subject compound as measured, for example, by XRPD. Thus, solid state of Selinexor described herein as substantially free of any other solid state forms would be understood to contain greater than about 80% (w/w), greater than about 90% (w/w), greater than about 95% (w/w), greater than about 98% (w/w), greater than about 99% (w/w), greater than about 99.5% (w/w) of the subject solid state form of Selinexor. Accordingly, in some embodiments of the disclosure, the described solid state forms of Selinexor may contain from about 1% to about 20% (w/w), from about 5% to about 20% (w/w), or from about 5% to about 10% (w/w) of one or more other solid state forms of the Selinexor.

As used herein unless stated otherwise, reference to % values are to wt %. This is based on an assumption that the solvent % in the various forms is measured in wt %).

As used herein, unless stated otherwise, XRPD peaks reported herein are measured using $CuK_\alpha$ radiation, $\lambda$=1.5418 Å. Preferably, the PXRD peaks for forms T1-3, T6, T7-10 and T15 are reported at $\lambda$=1.5406 Å at a temperature of 25±3° C., and the XRPD peaks for forms T4-5, T11-14 and T16-17 are reported herein are measured using $CuK_\alpha$ radiation at $\lambda$=1.5418 Å, at a temperature of 25±3° C. Alternatively, if an instrument with a different wavelength is used, for example, when using high resolution XRD method, such as synchrotron, the data may be corrected to wavelength of 1.5418 respectively.

As used herein, unless stated otherwise, $^{13}$C solid state NMR was measured at 400 MHz at room temperature at a spin rate of 11 kHz.

As used herein, unless stated otherwise, TGA was carried out at a heating rate of 10° C./min.

As used herein, the term "isolated" in reference to solid state forms of Selinexor of the present disclosure corresponds to solid state forms of Selinexor that is physically separated from the reaction mixture in which it is formed.

A thing, e.g., a reaction mixture, may be characterized herein as being at, or allowed to come to "room temperature", often abbreviated "RT." This means that the temperature of the thing is close to, or the same as, that of the space, e.g., the room or fume hood, in which the thing is located. Typically, room temperature is from about 20° C. to about 30° C., about 22° C. to about 27° C., or about 25° C.

A process or step may be referred to herein as being carried out "overnight." This refers to a time interval, e.g., for the process or step, that spans the time during the night, when that process or step may not be actively observed. This time interval is from about 8 to about 20 hours, about 10 to about 18 hours, or about 16 hours.

As used herein, the expression "wet crystalline form" refers to a polymorph that was not dried using any conventional techniques to remove residual solvent. Examples for such conventional techniques can be, but not limited to, evaporation, vacuum drying, oven drying, drying under nitrogen flow, etc.

As used herein, the expression "dry crystalline form" refers to a polymorph that was dried using any conventional techniques to remove residual solvent. Examples of such conventional techniques can be, but are not limited to, evaporation, vacuum drying, oven drying, drying under nitrogen flow, etc.

As used herein, and unless stated otherwise, the term "anhydrous" in relation to crystalline Selinexor relates to crystalline Selinexor which does not include any crystalline water (or other solvents) in a defined, stoichiometric amount within the crystal. Moreover, an "anhydrous" form does not contain more than about 1% (w/w) of either water or organic solvents as measured for example by TGA, by Karl Fischer Titration or by using other acceptable techniques.

The term "solvate", as used herein and unless indicated otherwise, refers to a crystal form that incorporates a solvent in the crystal structure. When the solvent is water, the solvate is often referred to as a "hydrate." The solvent in a solvate may be present in either a stoichiometric or in a non-stoichiometric amount. Stoichiometric of one water molecule within the crystal structure is defined as a "monohydrate".

The amount of solvent employed in a chemical process, e.g., a reaction or crystallization, may be referred to herein as a number of "volumes" or "vol" or "V." For example, a material may be referred to as being suspended in 10 volumes (or 10 vol or 10V) of a solvent. In this context, this expression would be understood to mean milliliters of the solvent per gram of the material being suspended, such that suspending 5 grams of a material in 10 volumes of a solvent means that the solvent is used in an amount of 10 milliliters of the solvent per gram of the material that is being suspended or, in this example, 50 mL of the solvent. In another context, the term "v/v" may be used to indicate the number of volumes of a solvent that are added to a liquid mixture based on the volume of that mixture. For example, adding methyl tert-butyl ether (MTBE) (1.5 v/v) to a 100 ml reaction mixture would indicate that 150 mL of MTBE was added.

As used herein the term non-hygroscopic in relation to crystalline Selinexor refers to less than about 0.2% (w/w) absorption of water at about 25° C. and about 80% relative humidity (RH) by the crystalline Selinexor as determined for example by TGA, by Karl Fischer Titration or by using other acceptable techniques. Water can be for example atmospheric water.

As used herein, the term "reduced pressure" refers to a pressure of about 10 mbar to about 50 mbar.

The present disclosure comprises a crystalline form of Selinexor designated as Form T1. The crystalline Form T1 of Selinexor can be characterized by data selected from one or more of the following: an XRPD pattern having peaks 10.2, 16.9, 21.1, 21.5, 22.7 and 26.7 degrees 2-theta±0.2 degrees 2-theta; an XRPD pattern as depicted in FIG. 1; and combinations of these data. Crystalline Form T1 of Selinexor may be further characterized by an XRPD pattern having peaks at 10.2, 16.9, 21.1, 21.5, 22.7 and 26.7-degrees 2-theta±0.2 degrees 2-theta, and also having one, two, three, four or five additional peaks selected from 5.8, 19.2, 19.7, 23.5 and 24.3 degrees two theta±0.2 degrees two theta.

Crystalline Form T1 of Selinexor may be characterized by each of the above characteristics alone/or by all possible combinations, e.g. by XRPD pattern having peaks at 10.2, 16.9, 21.1, 21.5, 22.7, and 26.7 degrees 2-theta±0.2 degrees 2-theta and an XRPD pattern as depicted in FIG. 1. Crystalline Selinexor form T1 may be characterized as 2-Butanol solvate, preferably as mono solvate of 2-Butanol. In certain embodiments, form T1 may contain from about 12% to about 16% by weight—of 2-butanol, specifically about 14% of 2-butanol.

In one embodiment of the present disclosure, form T1 is isolated.

In another embodiment of the present disclosure, form T1 of selinexor is polymorphically pure.

The present disclosure comprises a crystalline form of Selinexor designated as Form T2. The crystalline Form T2 of Selinexor can be characterized by data selected from one or more of the following: an XRPD pattern having peaks at 5.4, 15.9, 22.5, 22.8 and 24.6 degrees 2-theta±0.2 degrees 2-theta; an XRPD pattern as depicted in FIG. 2; and combinations of these data. Crystalline Form T2 of Selinexor may be further characterized by an XRPD pattern having peaks at 5.4, 15.9, 22.5, 22.8 and 24.6 degrees 2-theta±0.2 degrees 2-theta, and also having one, two, three, four or five additional peaks selected from 9.8, 14.4, 21.9, 23.9 and 27.1 degrees two theta±0.2 degrees two theta.

Crystalline Form T2 of Selinexor may be characterized by each of the above characteristics alone/or by all possible combinations, e.g. by XRPD pattern having peaks at 5.4, 15.9, 22.5, 22.8 and 24.6 degrees 2-theta±0.2 degrees 2-theta and an XRPD pattern as depicted in FIG. 2.

Crystalline Selinexor form T2 may be characterized as Isoamylalcohol solvate, preferably monosolvate of Isoamylalcohol. Crystalline Selinexor form T2 may be characterized also as mono solvate of Isoamylalcohol. In certain embodiments, form T2 may contain from about 14% to about 18% of Isoamylalcohol, specifically about 16% of Isoamylalcohol.

In one embodiment of the present disclosure, form T2 is isolated.

In another embodiment of the present disclosure, form T2 of selinexor is polymorphically pure.

The present disclosure comprises a crystalline form of Selinexor designated as Form T3. The crystalline Form T3 of Selinexor can be characterized by data selected from one or more of the following: an XRPD pattern having peaks at 5.7, 10.6, 15.3, 16.7, 22.6 and 23.6 degrees 2-theta±0.2 degrees 2-theta; an XRPD pattern as depicted in FIG. 3; and combinations of these data. Crystalline Form T3 of Selinexor may be further characterized by an XRPD pattern having peaks at 5.7, 10.6, 15.3, 16.7, 22.6 and 23.6 degrees 2-theta±0.2 degrees 2-theta, and also having one, two, three or four additional peaks selected from 11.9, 14.5, 20.7 and 26.4 degrees two theta±0.2 degrees two theta.

Crystalline Form T3 of Selinexor may be characterized by each of the above characteristics alone/or by all possible combinations, e.g. by XRPD pattern having peaks at 5.7, 10.6, 15.3, 16.7, 22.6, 23.6 degrees 2-theta±0.2 degrees 2-theta and an XRPD pattern as depicted in FIG. 3.

Crystalline Selinexor Form T3 can be characterized as Isobutanol solvate, preferably mono solvate of Isobutanol. In certain embodiments, form T3 may contain from about 12% to about 16% of Isobutanol, specifically about 14% of Isobutanol.

In one embodiment of the present disclosure, form T3 is isolated.

In another embodiment of the present disclosure, form T3 of selinexor is polymorphically pure.

The present disclosure comprises a crystalline form of Selinexor designated as Form T4. The crystalline Form T4 of Selinexor can be characterized by data selected from one or more of the following: an XRPD pattern having peaks at 5.9, 11.8, 12.9, 18.7, and 24.0 degrees 2-theta±0.2 degrees 2-theta; an XRPD pattern as depicted in FIG. 4; and combinations of these data. Crystalline Form T4 of Selinexor may be further characterized by an XRPD pattern having peaks at 5.9, 11.8, 12.9, 18.7, and 24.0 degrees 2-theta±0.2 degrees 2-theta, and also having one, two or three additional peaks selected from 16.3, 20.5 and 21.3 degrees two theta±0.2 degrees two theta. Crystalline Form T4 of Selinexor may be characterized by each of the above characteristics alone/or by all possible combinations, e.g. by XRPD pattern having peaks at 5.9, 11.8, 12.9, 18.7, and 24.0 degrees 2-theta±0.2 degrees 2-theta and an XRPD pattern as depicted in FIG. 4. Crystalline Form T4 of Selinexor can be characterized as Ethanol solvate and/or Hydrate. In some embodiments, form T4 of selinexor may contain from about 6% to about 9% of ethanol and/or from about 1% to about 3% of water. Preferably about 7% of ethanol and/or about 1.5% of water.

In one embodiment of the present disclosure, form T4 is isolated.

In another embodiment of the present disclosure, form T4 of selinexor is polymorphically pure.

The present disclosure comprises a crystalline form of Selinexor designated as Form T5. The crystalline Form T5 of Selinexor can be characterized by data selected from one or more of the following: an XRPD pattern having peaks at 6.1, 12.9, 27.0, 27.4 and 27.7 degrees 2-theta±0.2 degrees 2-theta; an XRPD pattern as depicted in FIG. 5; and combinations of these data. Crystalline Form T5 of Selinexor may be further characterized by data selected from an XRPD pattern having peaks at 6.1, 12.9, 27.0, 27.4 and 27.7 degrees 2-theta±0.2 degrees 2-theta, and also having one, two, three, four or five additional peaks selected from 11.6, 11.9, 12.3, 22.4 and 32.3 degrees two theta±0.2 degrees two theta.

Crystalline Form T5 of Selinexor may be characterized by each of the above characteristics alone/or by all possible combinations, e.g. by XRPD pattern having peaks at 6.1, 12.9, 27.0, 27.4 and 27.7 degrees 2-theta±0.2 degrees 2-theta and an XRPD pattern as depicted in FIG. 5. Crystalline Selinexor form T5 may be characterized as 1,4 Dioxane solvate and/or hydrate. In some embodiments, form T5 of selinexor may contain from about 3% to about 6% of 1,4 Dioxane and/or from about 2% to about 5% of water. Preferably about 4% of 1,4 Dioxane and/or about 3% of water.

In one embodiment of the present disclosure, form T5 is isolated.

In another embodiment of the present disclosure, form T5 of selinexor is polymorphically pure.

The present disclosure comprises a crystalline form of Selinexor designated as Form T6. The crystalline Form T6 of Selinexor can be characterized by data selected from one or more of the following: an XRPD pattern having peaks at 13.0, 13.7, 20.1, 23.2, 23.9 and 27.7 degrees 2-theta±0.2 degrees 2-theta; an XRPD pattern as depicted in FIG. 6; and combinations of these data. Crystalline Form T6 of Selinexor may be further characterized by an XRPD pattern having peaks at 13.0, 13.7, 20.1, 23.2, 23.9 and 27.7 degrees 2-theta±0.2 degrees 2-theta, and also having one, two, three, four or five additional peaks selected from 5.4, 10.9, 21.2, 26.2 and 27.1 degrees two theta±0.2 degrees two theta.

Crystalline Form T6 of Selinexor may be characterized by each of the above characteristics alone/or by all possible combinations, e.g. by XRPD pattern having peaks at 13.0, 13.7, 20.1, 23.2, 23.9 and 27.7 degrees 2-theta±0.2 degrees 2-theta and an XRPD pattern as depicted in FIG. 6. Crystalline Selinexor form T6 may be characterized as Isopropanol (IPA) solvate, preferably mono IPA solvate. In certain embodiments, form T6 may contain from about 9% to about 13% of IPA, specifically about 10% of IPA.

In one embodiment of the present disclosure, form T6 is isolated.

In another embodiment of the present disclosure, form T6 of selinexor is polymorphically pure.

The present disclosure comprises a crystalline form of Selinexor designated as Form T7. The crystalline Form T7 of Selinexor can be characterized by data selected from one or more of the following: an XRPD pattern having peaks at 15.1, 15.5, 21.6, 24.0 and 26.4 degrees 2-theta±0.2 degrees 2-theta; an XRPD pattern as depicted in FIG. 7; and combinations of these data. Crystalline Form T7 of Selinexor may be further characterized by an XRPD pattern having peaks at 15.1, 15.5, 21.6, 24.0 and 26.4 degrees 2-theta±0.2 degrees 2-theta, and also having one, two, three, four or five additional peaks selected from 16.2, 18.3, 23.3, 30.4 and 34.3 degrees two theta±0.2 degrees two theta.

Crystalline Form T7 of Selinexor may be characterized by each of the above characteristics alone/or by all possible combinations, e.g. by XRPD pattern having peaks 15.1, 15.5, 21.6, 24.0 and 26.4 degrees 2-theta±0.2 degrees 2-theta and an XRPD pattern as depicted in FIG. 7. Crystalline Selinexor form T7 can be also characterizes as Methanol solvate, more preferably as a monomethanol solvate. In certain embodiments, form T7 may contain from about 4% to about 8% of Methanol, specifically about 6% of Methanol.

In one embodiment of the present disclosure, form T7 is isolated.

In another embodiment of the present disclosure, form T7 of selinexor is polymorphically pure.

The present disclosure comprises a crystalline form of Selinexor designated as Form T8. The crystalline Form T8 of Selinexor can be characterized by data selected from one or more of the following: an XRPD pattern having peaks at 6.0, 13.4, 17.6, 19.6, and 24.9 degrees 2-theta±0.2 degrees 2-theta; an XRPD pattern as depicted in FIG. 8; a solid state $^{13}$C-NMR spectrum having characteristic peaks at 107.5, 126.0, 132.2, 141.5, 151.7 and 157.9 ppm±0.2 ppm; a solid state $^{13}$C-NMR spectrum having the following chemical shift absolute differences from a reference peak at 154.1 ppm±2 ppm of 46.6, 28.1, 21.9, 12.6, 2.4 and 3.8 ppm±0.1 ppm; a solid state $^{13}$C-NMR spectrum as depicted in FIG. 18 or 19 or 20; and combinations of these data.

Crystalline Form T8 of Selinexor may be further characterized by an XRPD pattern having peaks at 6.0, 13.4, 17.6, 19.6, and 24.9 degrees 2-theta±0.2 degrees 2-theta, and also having one, two, three, four or five additional peaks selected from 15.3, 20.8, 23.3, 26.4 and 29.6 degrees two theta±0.2 degrees two theta;

Crystalline Form T8 of Selinexor may be characterized by each of the above characteristics alone/or by all possible combinations, e.g. by XRPD pattern having peaks at 6.0, 13.4, 17.6, 19.6, and 24.9 degrees 2-theta±0.2 degrees 2-theta and an XRPD pattern as depicted in FIG. 8.

In another embodiment Crystalline Selinexor form T8 may be characterized as a hydrate, preferably a monohydrate.

Crystalline Selinexor T8 may contain from about 3% to about 5% of water, preferably about 4% of water, for example as measured by Karl Fischer.

In one embodiment of the present disclosure, form T8 is isolated.

In another embodiment of the present disclosure, form T8 of selinexor is polymorphically pure.

As discussed above, depending on which other solid state form it is compared with, Form T8 of Selinexor may according to the present disclosure may have advantageous properties selected from at least one of: chemical or polymorphic purity, flowability, solubility, dissolution rate, bioavailability, morphology or crystal habit, stability—such as chemical stability as well as thermal and mechanical stability with respect to polymorphic conversion, stability towards dehydration and/or storage stability, a lower degree of hygroscopicity, low content of residual solvents and advantageous processing and handling characteristics such as compressibility, or bulk density. Particularly, crystalline Form T8 of Selinexor of the present disclosure exhibits for example enhanced solubility in aqueous medium at pH=1.2 (HCl buffer), 4.5 (acetate buffer) and at pH 6.8 (phosphate buffer) in comparison with Form A of selinexor disclosed in U.S. Pat. No. 8,999,996. The increased solubility of Form T8 of Selinexor is particularly advantageous, as Selinexor Form A is practically insoluble in such a medium. The increased solubility of Form T8 of Selinexor may enhance bioavailability of the API.

The present disclosure comprises a crystalline form of Selinexor designated as Form T9. The crystalline Form T9 of Selinexor can be characterized by data selected from one or more of the following: an XRPD pattern having peaks at 3.2, 11.8, 14.5, 15.6, 16.8 and 18.0 degrees 2-theta±0.2 degrees 2-theta; an XRPD pattern as depicted in FIG. 9; and combinations of these data. Crystalline Form T9 of Selinexor may be further characterized by an XRPD pattern having peaks at 3.2, 11.8, 14.5, 15.6, 16.8 and 18.0 degrees 2-theta±0.2 degrees 2-theta, and also having one, two, three or four additional peaks selected from 20.0, 22.0, 23.9 and 25.4 degrees two theta±0.2 degrees two theta.

Crystalline Form T9 of Selinexor may be characterized by each of the above characteristics alone/or by all possible combinations, e.g. by XRPD pattern having peaks at 3.2, 11.8, 14.5, 15.6, 16.8 and 18.0 degrees 2-theta±0.2 degrees 2-theta and an XRPD pattern as depicted in FIG. 9. Crystalline Selinexor form T9 may be characterized as a hydrate, preferably a dihydrate. Selinexor form T9 may contain from about 6% to about 8% of water, as determined for example by Karl Fischer titration.

In one embodiment of the present disclosure, form T9 is isolated.

In another embodiment of the present disclosure, form T9 of selinexor is polymorphically pure.

The present disclosure comprises Selinexor designated as Form T10. Selinexor Form T10 can be characterized by data selected from one or more of the following: an XRPD pattern having peaks at 7.4, 10.6, 11.7, 12.8, 15.4 and 18.2 degrees 2-theta±0.2 degrees 2-theta; an XRPD pattern as depicted in FIG. 10; and combinations of these data. Selinexor form T10 may be further characterized by an XRPD pattern having peaks at 7.4, 10.6, 11.7, 12.8, 15.4 and 18.2 degrees 2-theta±0.2 degrees 2-theta, and also having one, two, three or four additional peaks selected from 3.7, 11.1, 21.3 and 24.5 degrees two theta±0.2 degrees two theta.

Selinexor form T10 may be characterized by each of the above characteristics alone/or by all possible combinations, e.g. by XRPD pattern having peaks at 7.4, 10.6, 11.7, 12.8, 15.4 and 18.2 degrees 2-theta±0.2 degrees 2-theta and an XRPD pattern as depicted in FIG. 10. Selinexor form T10 may be characterized as anhydrous form.

The present disclosure comprises Selinexor designated as Form T11. Selinexor Form T11 can be characterized by data selected from one or more of the following: an XRPD pattern having peaks at 9.8, 16.4, 20.4, 20.9, 25.0 and 25.5 degrees 2-theta±0.2 degrees 2-theta; an XRPD pattern as depicted in FIG. 11; and combinations of these data. Selinexor form T11 may be further characterized by an XRPD pattern having peaks at 9.8, 16.4, 20.4, 20.9, 25.0 and 25.5 degrees 2-theta±0.2 degrees 2-theta, and also having one, two, three, four or five additional peaks selected from 11.2, 13.4, 18.3, 22.5 and 23.3 degrees two theta±0.2 degrees two theta.

Selinexor form T11 may be characterized by each of the above characteristics alone/or by all possible combinations, e.g. by XRPD pattern having peaks at 9.8, 16.4, 20.4, 20.9, 25.0 and 25.5 degrees 2-theta±0.2 degrees 2-theta and an XRPD pattern as depicted in FIG. 11. Selinexor form T11 may be characterized as 2-Methoxyethanol and/or water form. In some embodiments, form T11 of selinexor may contain from about 3% to about 7% of 2-Methoxyethanol and/or from about 1% to about 3% of water. Preferably about 5% of 2-Methoxyethanol and/or about 2% of water.

In one embodiment of the present disclosure, form T11 is isolated.

In another embodiment of the present disclosure, form T11 of selinexor is polymorphically pure.

The present disclosure comprises Selinexor designated as Form T12. Selinexor Form T12 can be characterized by data selected from one or more of the following: an XRPD pattern having peaks at 3.5, 7.1, 9.6, 18.9, 19.3 and 25.8 degrees 2-theta±0.2 degrees 2-theta; an XRPD pattern as depicted in FIG. 12; and combinations of these data. Selinexor form T12 may be further characterized by an XRPD pattern having peaks at 3.5, 7.1, 9.6, 18.9, 19.3 and 25.8 degrees 2-theta±0.2 degrees 2-theta, and also having one, two, three, four or five additional peaks selected from 10.6, 10.9, 17.7, 20.3 and 20.9 degrees two theta±0.2 degrees two theta.

Selinexor form T12 may be characterized by each of the above characteristics alone/or by all possible combinations, e.g. by XRPD pattern having peaks at 3.5, 7.1, 9.6, 18.9, 19.3 and 25.8 degrees 2-theta±0.2 degrees 2-theta and an XRPD pattern as depicted in FIG. 12. Selinexor form T12 may be characterized as Methyl ethyl ketone (MEK) and/or hydrate form. In some embodiments, form T12 of selinexor may contain from about 4% to about 8% of MEK and/or from about 1% to about 3% of water, preferably about 6% of MEK and/or about 1.5% of water.

In one embodiment of the present disclosure, form T12 is isolated.

In another embodiment of the present disclosure, form T12 of selinexor is polymorphically pure.

The present disclosure comprises Selinexor designated as Form T13. Selinexor Form T13 can be characterized by data selected from one or more of the following: an XRPD pattern having peaks at 4.2, 8.3, 11.4, 14.0, 15.0 and 23.0 degrees 2-theta±0.2 degrees 2-theta; an XRPD pattern as depicted in FIG. 13; and combinations of these data. Selinexor form T13 may be further characterized by an XRPD pattern having peaks at 4.2, 8.3, 11.4, 14.0, 15.0 and 23.0 degrees 2-theta±0.2 degrees 2-theta, and also having one, two, three or four additional peaks selected from 10.1, 14.6, 18.8 and 25.7 degrees two theta±0.2 degrees two theta.

Selinexor form T13 may be characterized by each of the above characteristics alone/or by all possible combinations, e.g. by XRPD pattern having peaks at 4.2, 8.3, 11.4, 14.0, 15.0 and 23.0 degrees 2-theta±0.2 degrees 2-theta and an XRPD pattern as depicted in FIG. 13. Selinexor form T13 may be characterized as Acetophenone solvate. In some embodiments, form T13 of selinexor may contain from about 18% to about 22% of Acetophenone, preferably about 20% of Acetophenone.

In one embodiment of the present disclosure, form T13 is isolated.

In another embodiment of the present disclosure, form T13 of selinexor is polymorphically pure.

The present disclosure comprises Selinexor designated as Form T14. Selinexor Form T14 can be characterized by data selected from one or more of the following: an XRPD pattern having peaks at 7.6, 9.2, 10.0, 17.4, 19.0 and 22.9 degrees 2-theta±0.2 degrees 2-theta; an XRPD pattern as depicted in FIG. 14; and combinations of these data. Selinexor form T14 may be further characterized by an XRPD pattern having peaks at 7.6, 9.2, 10.0, 17.4, 19.0 and 22.9 degrees 2-theta±0.2 degrees 2-theta, and also having one, two, three or four additional peaks selected from 17.8, 21.2, 25.0 and 27.6 degrees two theta±0.2 degrees two theta.

Selinexor form T14 may be characterized by each of the above characteristics alone/or by all possible combinations, e.g. by XRPD pattern having peaks at 7.6, 9.2, 10.0, 17.4, 19.0 and 22.9 degrees 2-theta±0.2 degrees 2-theta and an XRPD pattern as depicted in FIG. 14. Selinexor form T14 may be characterized as N,N-Dimethyl Formamide solvate. In some embodiments, form T14 of selinexor may contain from about 23% to about 27% of N,N-Dimethyl Formamide. Preferably about 25% to about 26% of N,N-Dimethyl Formamide.

In one embodiment of the present disclosure, form T14 is isolated.

In another embodiment of the present disclosure, form T14 of selinexor is polymorphically pure.

The present disclosure comprises Selinexor designated as Form T15. Selinexor Form T15 can be characterized by data selected from one or more of the following: an XRPD pattern having peaks at 6.0, 11.2, 13.6, 21.4, 22.4 and 26.9 degrees 2-theta±0.2 degrees 2-theta; an XRPD pattern as depicted in FIG. 15; and combinations of these data. Selinexor form T15 may be further characterized by an XRPD pattern having peaks at 6.0, 11.2, 13.6, 21.4, 22.4 and 26.9 degrees 2-theta±0.2 degrees 2-theta, and also having one, two, three or four additional peaks selected from 10.0, 16.2, 20.4 and 25.0 degrees two theta±0.2 degrees two theta.

Selinexor form T15 may be characterized by each of the above characteristics alone/or by all possible combinations, e.g. by XRPD pattern having peaks at 6.0, 11.2, 13.6, 21.4, 22.4 and 26.9 degrees 2-theta±0.2 degrees 2-theta and an XRPD pattern as depicted in FIG. 15. Selinexor form T15 may be characterized as Di Acetic acid solvate. In some embodiments, form T15 of selinexor may contain from about 22% to about 27% of acetic acid. Preferably about 24% to about 26% of acetic acid.

In one embodiment of the present disclosure, form T15 is isolated.

In another embodiment of the present disclosure, form T15 of selinexor is polymorphically pure.

The present disclosure comprises Selinexor designated as Form T16. Selinexor Form T16 can be characterized by data selected from one or more of the following: an XRPD pattern having peaks at 4.8, 7.8, 9.5, 10.8 and 22.2 degrees 2-theta±0.2 degrees 2-theta; an XRPD pattern as depicted in FIG. 16; and combinations of these data. Selinexor form T16 may be further characterized by an XRPD pattern having peaks at 4.8, 7.8, 9.5, 10.8 and 22.2 degrees 2-theta±0.2 degrees 2-theta, and also having one, two, three or four additional peaks selected from 15.7, 19.2, 25.6 and 26.8 degrees two theta±0.2 degrees two theta.

Selinexor form T16 may be characterized by each of the above characteristics alone/or by all possible combinations, e.g. by XRPD pattern having peaks at 4.8, 7.8, 9.5, 10.8 and 22.2 degrees 2-theta±0.2 degrees 2-theta and an XRPD pattern as depicted in FIG. 16. Selinexor form T16 may be characterized as mono acetic acid solvate. In some embodiments, form T16 of selinexor may contain from about 8% to about 13% of acetic acid. Preferably about 10% to about 12% of acetic acid. Preferably about 11% of acetic acid.

In one embodiment of the present disclosure, form T16 is isolated.

In another embodiment of the present disclosure, form T16 of selinexor is polymorphically pure.

The present disclosure comprises Selinexor designated as Form T17. Selinexor Form T17 can be characterized by data selected from one or more of the following: an XRPD pattern having peaks at 9.1, 14.3, 20.9, 22.2 and 26.0 degrees 2-theta±0.2 degrees 2-theta; an XRPD pattern as depicted in FIG. 17; and combinations of these data. Selinexor form T17 may be further characterized by an XRPD pattern having peaks at 9.1, 14.3, 20.9, 22.2 and 26.0 degrees 2-theta±0.2 degrees 2-theta, and also having one, two, three or four additional peaks selected from 10.4, 18.3, 19.3 and 24.7 degrees two theta±0.2 degrees two theta.

Selinexor form T17 may be characterized by each of the above characteristics alone/or by all possible combinations, e.g. by XRPD pattern having peaks at 9.1, 14.3, 20.9, 22.2 and 26.0 degrees 2-theta±0.2 degrees 2-theta and an XRPD pattern as depicted in FIG. 17. Selinexor form T17 may be characterized as acetic acid solvate, more preferably as hemi acetic acid solvate. In some embodiments, form T17 of selinexor may contain from about 5% to about 9% of acetic acid. Preferably about 6% to about 8% of acetic acid, preferably, about 7% of acetic acid.

In one embodiment of the present disclosure, form T17 is isolated.

In another embodiment of the present disclosure, form T17 of selinexor is polymorphically pure.

The present disclosure also provides the use of any one or a combination of the solid state forms of Selinexor described above for preparing other solid state forms of Selinexor. For example, Selinexor forms T1, T6 and T17 can be used as intermediates for the purification of Selinexor.

In another embodiment, the present disclosure encompasses any one or a combination of the above described solid state forms of Selinexor and/or combinations thereof for use in the preparation of pharmaceutical compositions and/or formulations, optionally for the treatment of cancer.

In another embodiment, the present disclosure encompasses the use of any of the above described solid state forms of Selinexor and/or combinations thereof for the preparation of pharmaceutical compositions and/or formulations.

In yet another embodiment, the present disclosure encompasses pharmaceutical formulations comprising any one of the above described solid state forms of Selinexor and/or combinations thereof and optionally at least one pharmaceutically acceptable excipient.

The present disclosure encompasses processes to prepare said formulations of Selinexor comprising combining any one of the above solid state forms and/or combinations thereof and optionally at least one pharmaceutically acceptable excipient.

Any one of the solid state forms as defined herein and/or combinations thereof, as well as the pharmaceutical compositions or formulations thereof can be used as medicaments, particularly for the treatment of cancer.

The present disclosure also provides methods of treating cancer comprising administering a therapeutically effective amount of any one of the solid state forms of the present disclosure and/or combinations thereof, or at least one of the above pharmaceutical compositions or formulations, to a subject suffering from cancer, or otherwise in need of the treatment.

The present disclosure also provides the use of any one of the solid state forms of the present disclosure and/or combinations thereof, or at least one of the above pharmaceutical compositions or formulations for the manufacture of a medicament for treating cancer.

The present disclosure further provides the synthetic procedures for the preparation of Selinexor and intermediates thereof. The intermediates described herein and their process of preparation includes the following compounds, but not limited to 3-(3,5-bis(trifluoromethyl)phenyl)-1H-1,2,4-triazole (described here as SLN-103), (Z)-methyl 3-(3-(3,5-bis(trifluoromethyl)phenyl)-1H-1,2,4-triazol-1-yl)acrylate (described here as SLN-104) and (Z)-3-((3,5-bis(trifluoromethyl)phenyl)-1H-1,2,4-triazol-1-yl)acrylic acid (described here as SLN-105).

In one embodiment the present disclosure describes a process for preparation of 3-(3,5-bis(trifluoromethyl)phenyl)-1H-1,2,4-triazole (described here as SLN-103) according to the following scheme:

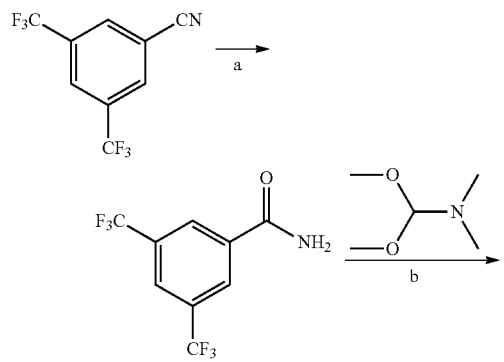

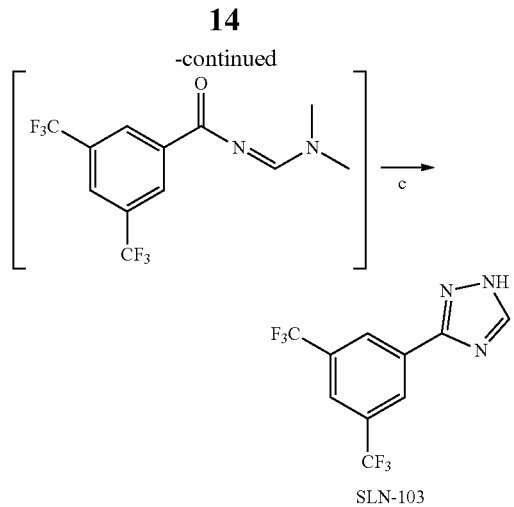

SLN-103

In one embodiment the present disclosure describes a process for preparation of 3-(3,5-bis(trifluoromethyl)phenyl)-1H-1,2,4-triazole (described here as SLN-103) comprising:
a) hydration of 3,5-bis(trifluoromethyl)benzonitrile to obtain 3,5-bis(trifluoromethyl)benzamide;
b) reacting 3,5-bis(trifluoromethylbenzamide with N,N-Dimethyl formamide dimethyl acetal to obtain N-((dimethylamino)methylene)-3,5-bis(trifluoromethyl)benzamide; and
c) reacting N-((dimethylamino)methylene)-3,5-bis(trifluoromethyl)benzamide with hydrazine hydrate.

The N-((dimethylamino)methylene)-3,5-bis(trifluoromethyl)benzamide can be isolated from the reaction mixture before step c). Preferably the N-((dimethylamino)methylene)-3,5-bis(trifluoromethyl)benzamide is not isolated from the reaction mixture, i.e. step c) is carried out without isolating the N-((dimethylamino)methylene)-3,5-bis(trifluoromethyl)benzamide from the reaction mixture.

Preferably, base is added to stage a). In one embodiment, the base can be selected from alkali metal carbonates and hydroxides, preferably can be selected from $Li_2CO_3$, $Na_2CO_3$, potassium carbonate, $CsCO_3$ or LiOH, sodium hydroxide, KOH, preferably the base is selected from potassium carbonate or sodium hydroxide.

Optionally, a solvent can be added to stage a). In one embodiment the solvent can be selected from polar protic solvents and polar aprotic solvents preferably methanol and DMSO or a mixture thereof.

Step a) is preferably conducted in the presence of hydrogen peroxide.

Optionally DMSO or a mixture of DMSO and methanol is used in stage (a).

Typically, the temperature in stage a) is at the range from 10 to 40° C., preferably at the range of 20-30° C.

Preferably, the solvent in stage b) can be selected from Polar aprotic solvents preferably N,N Dimethyl formamide.

Typically, acid is added in stage c). In one embodiment the added acid can be selected from carboxylic acid, preferably acetic acid.

Typically, the reaction is stage c) is heated at the temperature range from 40 to 90° C., preferably at temperature range from 50 to 55° C.

The novel procedure described above for the preparation of SLN-103 is much more preferable compared to known procedures. For example, procedure described in U.S. Pat. No. 8,999,996 (US'996) involves use of hazardous chemicals like Sodium Hydrosulfide, whereas current processes does not contain use of any sulfur compounds. Furthermore, the described process is associated with liberation of toxic fumes i.e. H2S gas during thioamide to triazole ring formation, while current process does not liberate any toxic fumes.

Moreover, the processes for SLN-103 as described in this disclosure involve mild reaction, by using low temperatures conditions e.g. 50-55° C., while the reaction conditions described in US'996 are harsh e.g. 90° C. Furthermore, minimum solvents content, e.g. from about 0.8 volumes to about 4 volumes, about 0.8 volumes to about 2 volumes, about 0.9 to about 1.5 volumes or about 0.9 to about 1.2 volumes, and particularly about 1 volume, compared to a typical ratio of 5 to 10 volumes, may be used for the reaction in novel process which allows economical process in terms of raw material costs and overall reactor occupancy.

In another embodiment the present disclosure describes the preparation of (Z)-methyl 3-(3-(3,5-bis(trifluoromethyl) phenyl)-1H-1,2,4-triazol-1-yl)acrylate (described here as SLN-104) according to the following scheme:

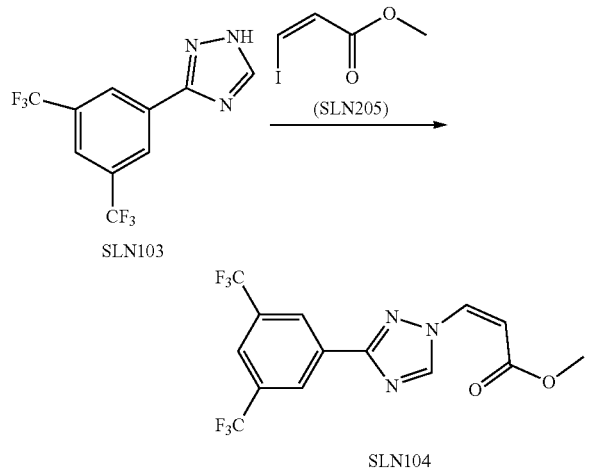

In another embodiment the present disclosure describes the preparation of (Z)-methyl 3-(3-(3,5-bis(trifluoromethyl) phenyl)-1H-1,2,4-triazol-1-yl)acrylate (described here as SLN-104) comprising:
  a) Providing a mixture comprising SLN-103, an alkali metal carbonate and 1,4-diazabicyclo[2.2.2] octane (DABCO);
  b) Adding Z-methyl iodoacrylate (SLN205) to produce SLN-104; and optionally
  c) purifying the SLN-104 by slurrying in a mixture of Ethyl acetate and Cyclohexane, cooling, filtering and drying.

Typically, the solvent used in stages a) and b) can be selected from polar aprotic solvents preferably selected from acetone, THF, acetonitrile and DMF. Preferably the solvent is selected from acetonitrile and/or DMF.

Preferably, the alkali metal carbonates in stage a) can be selected from potassium carbonate.

Preferably, the Z-methyl iodoacrylate is added slowly (e.g. dropwise), more preferably to maintain a temperature of between −5° C. to +5° C.

Preferably, after the reaction step (a), water can be added in order to precipitate the SLN-104. Preferably water is added to precipitate the SLN-104 completely.

Surprisingly, the yield of SLN-104 in this novel procedure increases drastically from 65%, as reported in US'996, to 88%. Furthermore, the innovator reported slow reaction rate and presence of 8% E-isomer in product even after purification, while in this novel process, the use of an alkali metal carbonate and particularly $K_2CO_3$ enabled faster reaction conversion which in-turn resulted with controlled E-isomer below 1.0% in the isolated product without any purification.

In another embodiment the present disclosure describes the preparation of (Z)-3-(3-(3,5-bis(trifluoromethyl)phenyl)-1H-1,2,4-triazol-1-yl)acrylic acid (described here as SLN-105) according to the following scheme:

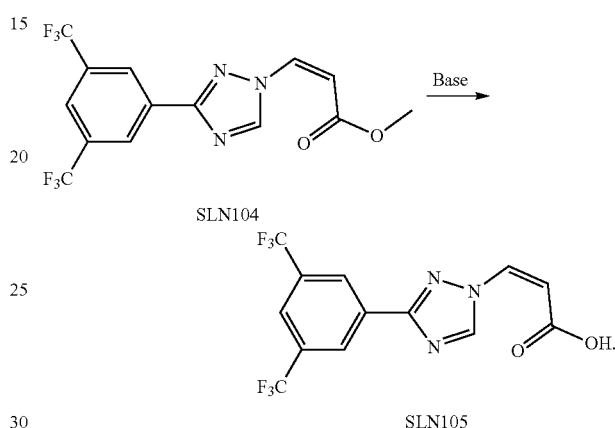

In another embodiment the present disclosure describes the preparation of (Z)-3-(3-(3,5-bis(trifluoromethyl)phenyl)-1H-1,2,4-triazol-1-yl)acrylic acid (described here as SLN-105) comprising: reacting SLN-104 with a base selected from alkali metal bases, in the presence of mixture of solvents.

Typically, the mixture of solvents can be selected from mixture of polar protic solvents, mixture of polar aprotic solvent and mixture thereof. Preferably the mixture of solvents is selected from mixture of methanol and water, ethanol and water, tert-butanol and water or mixture of methanol, THF and water. Preferably, mixture of tert-butanol and water.

The alkali metal base can particularly be selected from an alkali metal hydroxide, an alkali metal carbonate or alkali metal hydrogen carbonate. Particularly, the alkali metal base can be an alkali metal hydroxide. Typically, the alkali metal bases can be selected from an alkali metal hydroxide, particularly lithium hydroxide, sodium hydroxide and potassium hydroxide. Preferably, lithium hydroxide is used as the base. The alkali metal bases can also be selected from alkali metal carbonates or alkali metal hydrogen carbonates, which can particularly be selected from sodium carbonate, potassium carbonate, sodium hydrogen carbonate, and potassium hydrogen carbonate.

In another embodiment the process for preparation of SLN-105 is favored especially when the reaction mixture includes Tertiary butanol which (without wishing to be bound by theory) appears to restrict the transformation to undesired E isomer (only 0.66% in novel process). Furthermore, the isolated product has very high isomeric purity, hence purification step can be avoided.

In another aspect the present disclosure comprises a process for preparing Selinexor by coupling SLN-105 and 2-hydrazino Pyrazine according to following scheme:

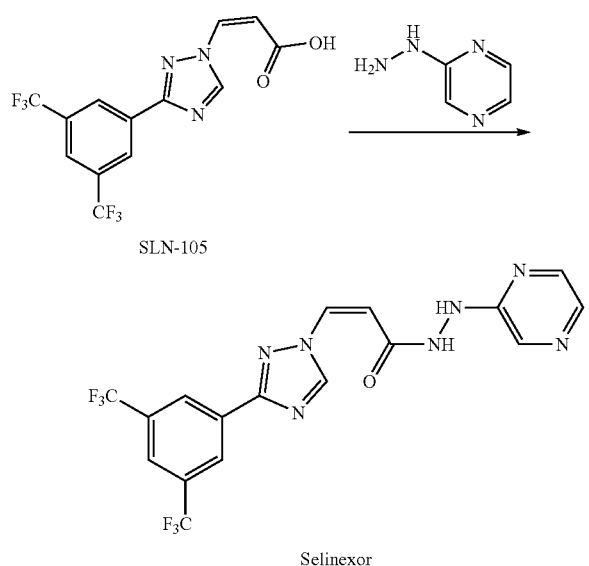

SLN-105

Selinexor

In another aspect the present disclosure comprises a process for preparing Selinexor by coupling SLN-105 and 2-hydrazino Pyrazine in the presence of 1-Ethyl-3-(3-dimethylaminopropyl) carbodiimide hydrochloride (EDC. HCl).

Typically the process is carried out in a solvent system comprising one or more polar solvents, preferably protic solvents (preferably $C_{1-6}$ alcohols, more preferably $C_{1-3}$ alcohols) and esters of alcohols (preferably $C_{1-6}$ esters of $C_{1-6}$ alcohols, more preferably $C_{1-3}$ esters of $C_{1-3}$ alcohols). Suitable solvents include but are not limited to acetonitrile and esters of alcohols or combinations thereof. Preferably the solvent is an alcohol, more preferably methanol.

In prior art processes, T3P (propyl phosphonic anhydride) is used as an amide coupling agent, which is expensive. Furthermore, low temperature (−40 to −20° C.) is required in this reaction, resulted only with low conversion (about 30 to 40%) to Selinexor. Surprisingly, the present novel procedure includes use of EDC. HCl which is commercially available and not expensive. Moreover, cryogenic condition is not required in novel reaction. Furthermore, very high reaction conversion is obtained herein (90-96%).

The present disclosure further comprises process for preparing Selinexor form T8, wherein Selinexor form T7 was stored at 40-90%, 45-80%, 45-70%, 45-55% and preferably about 50% relative humidity for 72 hr at 20° C.

The present disclosure further comprises process for the preparation of Selinexor form T8 comprising:
 a) providing a solution of Selinexor in methanol under heating;
 b) optionally purifying, preferably by treatment with charcoal and filtering;
 c) optionally reheating the filtrate in stage b) to dissolve the Selinexor; and
 d) cooling, and optionally filtering and drying the powder.

Preferably, cooling and filtering in stage d) is done under inert atmosphere, preferably under nitrogen.

The process for preparing Selinexor form T8 typically comprises precipitating selinexor from methanol. Preferably the process comprises precipitating selinexor by cooling a hot solution of selinexor in methanol. More preferably the process comprises cooling a hot solution of selinexor in methanol, wherein the hot solution is preferably at a temperature of 45-75° C. and more preferably 50-60° C. The solution typically contains a small amount of water. Preferably at least about 3.9 wt % (based on the weight of selinexor) of water is present. More preferably, water is present in the solution in an amount of from: 3.9-6 wt %, 3.9-5%, 3.9-5.8 wt % or 3.9-4.5 wt % (based on the weight of selinexor). The water can be present in the starting Selinexor, or sufficient water (e.g. at least about 3.9 wt % based on the weight of selinexor, or preferably from 3.9-6 wt %, 3.9-5 wt %, 3.9-5.8 wt % or 3.9-4.5 wt % based on the weight of selinexor) can be added to the solution to prepare form T8. Preferably the selinexor starting material contains at least about 3.9 wt % (based on the weight of selinexor) of water. More preferably the selinexor starting material contains from: 3.9-6 wt %, 3.9-5%, 3.9-5.8 wt % or 3.9-4.5 wt % (based on the weight of selinexor) of water.

Typically, the methanol volume used in stage a) is at the range of 3 to 10 vol, preferably at about 3 or 7 vol.

Preferably Selinexor is heated in stage a) to temperature range of 55-60° C. to get a clear solution.

Preferably step (d) is conducted in an inert atmosphere, preferably under nitrogen.

In another embodiment, Selinexor form T8 prepared by precipitation from methanol shows high chemical purity.

Typically, crystallization of selinexor in methanol shows high chemical purity.

As defined herein, "high purity" refers to chemical purity wherein at least about more than 99%, more than about 99.5% or more than about 99.9% Selinexor is measured by any technique described in the literature. e.g. by HPLC.

The present disclosure comprises isolation and purification of Selinexor using class III solvents, such as ethanol, methanol, etc.

Having described the disclosure with reference to certain preferred embodiments, other embodiments will become apparent to one skilled in the art from consideration of the specification. The disclosure is further illustrated by reference to the following examples describing in detail the preparation of the composition and methods of use of the disclosure. It will be apparent to those skilled in the art that many modifications, both to materials and methods, may be practiced without departing from the scope of the disclosure.

Analytical Methods
Analytical Method by HPLC
Chromatographic Conditions

| Column & Packing | Phenyl; 3.5 µm, 250×4.6 mm or equivalent | | |
|---|---|---|---|
| Eluent A | Water:Methanol (700:300v/v) + 1 mL HClO$_4$ 70% | | |
| Eluent B | Water:Methanol:Acetonitrile (200:400:400 v) + 1 mL HClO$_4$ 70% | | |
| | Time | Eluent A | Eluent B |
| Gradient | 0 | 60 | 40 |
| | 35 | 40 | 60 |
| | 40 | 30 | 70 |
| | 45 | 0 | 100 |
| | 50 | 0 | 100 |
| | 50.1 | 60 | 40 |
| Equilibration time | 10 min | | |
| Injection volume | 10 µL | | |
| Flow Rate | 1.0 mL/min | | |
| Detector | 245 nm (BW 4 nm) | | |
| Column temperature | 40° C. | | |
| Diluent | Water:Methanol (30:70 v/v) | | |

Test Solution—TS (1.0 mg/mL)

Accurately weigh and transfer about 50.0 mg of Sample into a 50.0 mL volumetric flask. Add about 10.0 mL of Methanol and sonicate to dissolve. Add about 20.0 mL of Diluent and sonicate.
Retention time: Selinexor: about 18 minute

| Stage | RRT |
|---|---|
| SLN-103 | 0.84 |
| Z-SLN | 1.00 |
| E-SLN | 1.07 |
| Methoxy impurity of SLN105 | 1.22 |
| Z-SLN 105 | 1.31 |
| E-SLN 105 | 1.44 |

X-Ray Powder Diffraction Method

The X-ray powder diffraction patterns in FIGS. 1-3 & 6, 7-10 & 15 were measured with BRUKER D8 Advance X-ray powder diffractometer, CuKα radiation (λ=1.5406 Å); Lynxeye XE detector, low amount PMMA sample holder with zero background plate was used. Prior to analysis, the samples were gently ground by means of mortar and pestle in order to obtain a fine powder. The ground sample was adjusted into a cavity of the sample holder and the surface of the sample was smoothed by means of a cover glass. Measurement parameters: Sample: Spin mode, rotation speed 30 rpm; Scan range: 2-40 degrees 2-theta; Scan mode: continuous; Step size: 0.05±0.005 degrees; Time per step: 0.5 sec; Divergence slit: V20.

The X-ray powder diffraction patterns in FIGS. 4 to 5 and FIGS. 11 to 14 and 16 to 17 were measured with X'Pert PRO PANalytical; CuKα radiation (λ=1.5418 Å); PIXcel detector; laboratory temperature 22-25° C.; The samples were gently ground by means of mortar and pestle in order to obtain a fine powder. Measurement parameters: Scan range) (°) 2.994-50.000, Step size (°): 0.0262606, Time per Step (s): 80.325, No. of steps: 1790, Scan mode: Continuous, without sample spinning.

Solid-state $^{13}$C NMR spectra were recorded with variable amplitude cross polarization, magic angle spinning and high power proton decoupling using a BRUKER Avance II+ spectrometer operating at 125 MHz and controlled temperature of 0° C. A probe using 4 mm o.d. zirconia rotors was employed. The operation conditions were: contact time 3 ms; acquisition time, recycle delay: 2 s, 5100 scans; spin rate: 11 kHz. Chemical shifts were referenced via a replacement sample of glycine (carboxyl carbon chemical shift assigned as 176.03 ppm relative to the signal of tetramethylsilane).

Thermogravimetric Analysis (TGA) Method

TGA measurements were performed on a Thermogravimetric analyzer TGA851e (Mettler Toledo). Alumina crucibles 70 µl were used for sample preparation. Usual sample weight was between 5 and 15 mg. Program parameters: temperature range at least 30-200° C.; heating rate 10° C./min; nitrogen flow 50 ml/min.

EXAMPLES

Selinexor can be prepared according to any procedure described in the literature such as Example 2 described in U.S. Pat. No. 8,999,996. Selinexor can be also prepared when using SLN-103 to produce SLN-104 that finally converts to SLN-105 which is the intermediate used in examples 9, 10, 29 and 30 for the preparation of Selinexor. This synthesis procedure is described in examples 16 & 26 (from SLN-103 to SLN-104) and examples 17 & 27 (from SLN-104 to SLN-105). Advantageously synthesis of SLN-103 is described in example 33.

Purification procedures for the preparation of Selinexor form T8 obtained in high purity are described in examples 31-32.

Selinexor forms A, C and D described in WO2016025904 can be used as a staring material for preparation of T1-T9, T11-T12, T13-T17 and for amorphous form. Forms A and C can be also prepared by examples 9-10 described below and/or by using any procedure described in the literature, such as in WO2016025904.

Example 1: Preparation of Selinexor Form T1

Selinexor (Form C) 0.20 gr was added to 0.6 ml of 2-Butanol at 20-25° C. and the obtained slurry was stirred for 24 hrs at 20-25° C. The obtained solid was filtered under vacuum and kept under suction for about 20 minutes at 20-25° C. to obtain 0.15 gr of Selinexor powder.

Example 2: Preparation of Selinexor Form T2

Selinexor (Form C) 0.20 gr was added to 1.2 ml of Isoamylalcohol at 20-25° C. and the obtained slurry was stirred for 24 hrs at 20-25° C. The obtained solid was filtered under vacuum and kept under suction for about 20 minutes at 20-25° C. to obtain 0.15 gr Selinexor powder.

Example 3: Preparation of Selinexor Form T3

Selinexor (Form C) 0.20 gr was added to 1 ml of Isobutanol at 20-25° C. and the obtained slurry was stirred for 3 days. The obtained solid was filtered under vacuum and kept under suction for about 20 minutes at 20-25° C. to obtain 0.14 gr Selinexor powder.

Example 4: Preparation of Selinexor form T4

Selinexor (Form A) 0.5 gr and 3.5 ml of absolute ethanol were added into flask, stirred for 30 min at 25° C. to obtain a thick slurry. After 30 min of stirring, the slurry was cooled to 0-5° C. and the solvent was distilled off under vacuum (less than 12 mbar) at 0-5° C. The obtained solid was dried at 0-5° C. for 2 hr under vacuum to obtain 0.5 gr of Selinexor.

Example 5: Preparation of Selinexor Form T5

Selinexor (Form A) 0.5 gr was dissolved in 5 ml of 1,4-Dioxane at 30-40° C. and maintained as a clear solution at 25-30° C. for 15 min. The solution was then cooled to 0-5° C. and the solvent was distilled off under vacuum (less than 10 mbar) at 0-5° C. The obtained solid was dried for 2 hr under vacuum at 0-5° C. to obtain 0.5 gr of Selinexor.

Example 6: Preparation of Selinexor Form T6

Selinexor (Form C) 0.2 gr was added to 1 ml of Isopropanol (IPA) at 20-25° C. and the slurry was stirred for 3 days at 20-25° C. The obtained solid was filtered under vacuum and kept under suction for about 20 minutes at 20-25° C. to obtain 0.13 gr of Selinexor.

Example 7a: Preparation of Selinexor Form T7

Selinexor (Form C) 0.5 gr was added to 2 ml of Methanol at 20-25° C. and the slurry was stirred for 7 days at 20-25°

C. The obtained solid was filtered under vacuum and kept under suction for about 20 minutes at 20-25° C. to obtain 0.3 gr of Selinexor.

Example 7b: Preparation of Selinexor Form T7

Selinexor (Form C) 0.5 gr was added to 4 ml of Methanol at 20-25° C. and the slurry was stirred for 24 hr at 20-25° C. The obtained solid was filtered under vacuum and kept under suction for about 20 minutes at 20-25° C. to obtain 0.3 gr of Selinexor.

Example 8: Preparation of Selinexor Form T8

Selinexor form T7 prepared by example 7 was kept open for 72 hr at 20° C. and under 50% RH to obtain Selinexor form T8.

Example 9: Preparation of Selinexor Form C

Charged (100 gm, 1.0 eq) (Z)-3-((3,5-bis(trifluoromethyl)phenyl)-1H-1,2,4-triazol-1-yl)acrylic acid (described here as SLN-105) in 0.6 L of DMF (N,N-Dimethyl Formamide) and cooled to 0-5° C. Charged 47.0 gm (1.5 eq) 1-(pyrazin-2-yl) hydrazine and 81.8 gm of EDC.HCl (1-Ethyl-3-(3-dimethylaminopropyl) carbodiimide hydrochloride) at 0-5° C. The reaction was stirred for 3 hr and the reaction completion was confirmed by HPLC. Once the reaction completed, quenched the reaction mass into a pre-chilled mixture consist 2.5 L of DMWater (Demineralized water) 0.5 L of 2-MethylTHF, 1.0 L of ethyl acetate and 0.25 L of Conc. Hydrochloric acid at 10-15° C. and stirred the reaction mass for 15 min. Settled and separated the organic layer. Collected aqueous layer and extracted by mixture 0.7 L of Ethyl acetate and 0.3 L of 2-Methyltetrahydrofuran at 20-25° C. Combined both the organic layers and washed with 5% (0.7 L) sodium bicarbonate solution. Collected the organic layer and charged 10.0 gm carbon (Norit CGP super, pH neutral), stirred for 15-30 min and filtered the organic layer through hyflo bed at 20-30° C. then washed with 0.2 L of Ethyl acetate. Collected final organic layer and concentrated under vacuum at 50-55° C. till no recovery of solvent then cooled reaction mass to 20-30° C. then charged 1.5 L of Acetonitrile to the reaction mass, heated to 70-75° to get clear solution then slowly cooled the clear solution over the period 2-3 hr to 20-30° C. and stirred for 30 min. Filtered the slurry and washed with 0.5 L of Acetonitrile. The filter cake (20-25% acetonitrile) was charged into 1.1 L of Acetonitrile and heated to 65-70° C. to get clear solution and slowly cooled the solution over the period of 2-3 hr to 20-30° C. then stirred the slurry for 30 min at 20-30° C. Filtered the slurry and washed with 0.5 L of Acetonitrile. The filtered cake was dried under vacuum at 65-70° C. to get 75 gm (60%) pure Selinexor Form C.

Example 10: Preparation of Selinexor Form A

Charged (100 gm, 1.0 eq) (Z)-3-((3,5-bis(trifluoromethyl)phenyl)-1H-1,2,4-triazol-1-yl)acrylic acid (described here as SLN-105) in 0.6 L of DMF (N,N-Dimethyl Formamide) and cooled to 0-5° C., charged 47.0 gm (1.5 eq) 1-(pyrazin-2-yl)hydrazine and 81.8 gm of EDC.HCl (1-Ethyl-3-(3-dimethylaminopropyl) carbodiimide hydrochloride) at 0-5° C. The reaction was stirred for 3 hr and the reaction completion was confirmed by HPLC. Once the reaction completed, quenched the reaction mass into a pre-chilled mixture consist 2.5 L of DMWater (Demineralized water), 0.5 L of 2-MethylTHF, 1.0 L of ethyl acetate and 0.25 L of Conc. Hydrochloric acid at 10-15° C. and stirred the reaction mass for 15 min. Settled and separated the organic layer. Collected aqueous layer and extracted by mixture 0.7 L of Ethyl acetate and 0.3 L of 2-Methyltetrahydrofuran at 20-25° C. Combined both the organic layers and washed with 5% (0.7 L) sodium bicarbonate solution. Collected the organic layer and charged 10.0 gm carbon (Norit CGP super, pH-neutral), stirred for 15-30 min and filtered through hyflo bed at 20-30° C. then washed with 0.2 L of Ethyl acetate. Collected final organic layer and concentrated under vacuum at 50-55° C. till no recovery of solvent then cooled reaction mass to 20-30° C. then charged 1.5 L of Acetonitrile to the reaction mass, heated to 70-75° to get clear solution. Slowly cooled the clear solution over the period of 2-3 hr to 20-30° C. and stirred for 30 min. Filtered and washed with 0.5 L of Acetonitrile. The filter cake (20-25% acetonitrile) was charged into 0.4 L of ethyl acetate and heated to 65-70° C. to get clear solution and slowly cooled the solution over the period of 1.5-2 hr to 20-30° C. stirred for 30 min then further cooled to 0-5° C., stirred the slurry for 60 min at 0-5° C. Filtered and washed with 0.1 L of ethyl acetate. The filtered cake was dried under vacuum at 50-55° C. to get 78 gm (62%) pure Selinexor Form A.

Example 11: Preparation of Selinexor Form T9

0.15 gr of Selinexor Form T4 was added in 2.5 ml of Demineralized water at 0-5° C. and the obtained slurry was stirred for 3 hrs at 0-5° C. The obtained solid was filtered under vacuum and kept for air tray dryer at 20-25° C. for 4 hours to obtain 0.1 gr Selinexor form T9.

Example 12: Preparation of Selinexor Form T9

0.15 gr of Selinexor Form T7 was added in 1.5 ml of Demineralized water at 0-5° C. and the obtained slurry was stirred for 6 hours at 0-5° C. The obtained solid was filtered under vacuum and kept under suction for about 120 minutes at 20-25° C. to obtain 0.1 gr of Selinexor form T9.

Example 13: Preparation of Selinexor Form T9

2 gr of Selinexor (Form A) was added in 5.0 ml acetone at 20-25° C. and stirred at 20-25° C. for 24 hrs to obtain saturated solution. The obtained solid was filtered and the saturated solution was collected. 2 ml of Demineralized water was taken into a single neck round bottom flask and cooled to 0-5° C. Then add 0.5 ml of the above prepared stock solution in acetone into the precooled Demineralized water. The obtained slurry was stirred for 30 min at 0-5° C. The obtained solid was filtered under vacuum and kept under suction for about 90 minutes at 20-25° C. to obtain 0.1 gr of Selinexor form T9.

Example 14: Preparation of Selinexor Form T10

Selinexor (Form T9) 0.15 gr was dried at 60° C. for 30 min in vacuum tray dryer to obtain 0.09 gr of Selinexor form T10.

Example 15: Preparation of Selinexor Form T10

Selinexor (Form T9) 0.025 gr was dried at 60° C. for 30 min in thermo gravimetric furnace under the nitrogen atmosphere to obtain Selinexor form T10.

Example 16: Synthesis Procedure from SLN-103 to SLN-104

Charged 100 gr (1.0 eq) of 3-(3,5-bis(trifluoromethyl)phenyl)-1H-1,2,4-triazole (described here as SLN-103) in 0.8 L of DMF. Charged Potassium Carbonate (61.4 gr, 1.25 eq) and stirred for 30 min. Charged 1,4-diazabicyclo[2.2.2]octane (DABCO) (49.7 gr, 1.25 eq) and cooled to −5 to −10° C., Slowly added solution of Z-methyl iodoacrylate (93.6 gr, 1.25 eq) in 0.2 L of DMF at −5 to −10° C. Stirred for 1 hrs. at −5 to −10° C. and monitored the content of unreacted SLN-103 (Limit of SLN-103 is NMT 1.0%) on by HPLC. After reaction completion charged pre-chilled water 5 L at 5-10° C., stirred for 1 hrs. at 5-10° C. Filtered and washed the wet-cake with 0.2 L of water. The wet-cake is purified by making a slurry in a solvent mixture of 0.1 L Ethyl acetate & 1.0 L Cyclohexane at 20-25° C. The slurry was cooled to 5-10° C., stirred for 30 mins, filtered and washed with cyclohexane 0.1 L at 20-25° C. The filtered wet-cake was dried under vacuum at 35-40° C. to get 105 gr of (Z)-methyl 3-(3-(3,5-bis(trifluoromethyl)phenyl)-1H-1,2,4-triazol-1-yl)acrylate (described here as SLN-104) (Yield: 81%) pure SLN-104 (Purity:—Z isomer 99.18%, E isomer 0.80%).

Example 17: Synthesis Procedure from SLN-104 to SLN-105

Charged (100 gr, 1.0 eq) SLN-104 (prepared according to example 16, or example 26) in a solvent mixture containing 0.5 L of water, 0.25 L of methanol & 0.15 L of THF. Charged Lithium hydroxide (45.8 gm, 4.0 eq) and stirred for 1 hour at 20-30° C. Monitor the content of unreacted SLN-104 (limit of SLN-104 is NMT 0.5%) by HPLC. After reaction completion, charged 0.5 L water to the reaction mass at 20-30° C. Slowly adjusted the PH~2 using 1:1 dilute HCl (0.1 L). Stirred for 1 hour at 20-30° C., and filtered and washed with 0.2 L of water. The filtered cake was dried under vacuum at 50-55° C. to get 93 gr (Yield: 96%) of pure (Z)-3-(3-(3,5-bis(trifluoromethyl)phenyl)-1H-1,2,4-triazol-1-yl)acrylic acid (described here as SLN-105) (Purity:—Z isomer 96.77%, E isomer 0.66%).

Example 18: Preparation of Selinexor Form T11

Selinexor (Form A) 0.5 gr was dissolved in 2.5 ml of 2-Methoxy ethanol at 25-30° C. and the clear solution was maintained at 25-30° C. for 15 min. Then the solution was cooled to 0-5° C. in 15 min and stirred for further 30 min at 0-5° C. The solvent was distilled off under vacuum at 0-5° C. for 24 hr. The solvent evaporation was very slow, the temperature was raised to 25° C. in 35 min and continued the distillation under vacuum (5-10 mbar) at 25° C. for an extra 4 hr. The obtained solid was dried at 25° C. for 4 hr under vacuum to obtain Selinexor form T11 (0.5 gr).

Example 19: Preparation of Selinexor Form T12

Selinexor (Form A) 0.5 gr was dissolved in 5 ml of Methyl ethyl ketone (MEK) at 20-25° C. and the clear solution was maintained at 25-30° C. for 30 min. The clear solution was filtered under vacuum at 25-30° C. and transferred into another flask. The solution was then cooled to 0-5° C. in 20 min. The solvent was distilled off under vacuum (less than 10 mbar) at 0-5° C. in 2 hr. The obtained solid was dried for 3 hr under vacuum at 0-5° C. to obtain Selinexor form T12 (0.4 gr).

Example 20: Preparation of Amorphous Selinexor

Selinexor (form C) 5.0 gr and 100 ml of methanol was added in flask and stirred for 10 min at 50° C. to obtain a clear solution. The solution was distilled off under vacuum (less than 12 mbar) at 50° C. in 20 min. The obtained solid was dried at 50° C. for 2 hr under vacuum to obtain amorphous Selinexor (4.5 gr). The measured Tg: 74.39° C. (Onset temperature).

Example 21: Preparation of Selinexor Form T13

Selinexor (Form C) 5.0 gr was added in 10.0 ml acetophenone at 20-25° C. and stirred at 20-25° C. for 24 hrs to get a saturated solution. The obtained solid was filtered and the saturated solution was collected.

Taken 4 ml of pentane into a vial and cool it to 0-5° C. Add 1.0 ml of the above prepared API stock solution in acetophenone into the precooled pentane and the obtained slurry was stirred for 30 min at 0-5° C. The obtained solid was filtered under vacuum and kept under suction for about 15 minutes at 20-25° C. to obtain 0.1 gr of form T13.

Example 22: Preparation of Selinexor Form T14

Selinexor (Form A) 5.0 gr was added to 10.0 ml N,N-Dimethylformamide (DMF) at 20-25° C. and stirred at 20-25° C. for 30 min to prepare saturated solution. The obtained solid was filtered and the saturated solution was collected.

Taken 4 ml of heptane into a vial and cool it to 0-5° C. Add 1.0 ml above prepared API stock solution in N,N-Dimethylformamide into precooled heptane and the obtained slurry was kept for stirring for 24 hrs at 0-5° C. The obtained solid was filtered under vacuum and kept under suction for about 15 minutes at 20-25° C. to obtain 0.1 gr of Selinexor form T14.

Example 23: Preparation of Selinexor Form T15

Selinexor (Form D) 1.0 gr was added in 2 ml of acetic acid at 20-25° C. and the obtained slurry was stirred for 24 hrs at 20-25° C. The obtained solid was filtered under vacuum and kept under suction for about 20 minutes at 20-25° C. to obtain 0.85 gr of Selinexor form T15.

Example 24: Preparation of Selinexor Form T16

Selinexor (Form A) 5.0 gr was added in 10.0 ml Acetic acid at 20-25° C. and stirred at 20-25° C. for 30 min to prepare saturated solution. The obtained solid was filtered and the saturated solution was collected.

Taken 4 ml of methyl cyclohexane into a vial and cool it to 0-5° C. Add 1.0 ml of the above prepared API stock solution in acetic acid into the precooled methyl cyclohexane and the obtained slurry was kept for stirring for 30 min at 0-5° C. The obtained solid was filtered under vacuum and kept under suction for about 15 minutes at 20-25° C. to obtain 0.4 gr form T16.

Example 25: Preparation of Selinexor Form T17

Selinexor (Form A) 0.3 gr was dissolved in 15 ml of acetic acid at 70° C. and the clear solution was maintained at 70° C. for 30 min. The clear solution was filtered under vacuum at 25-30° C. and transferred into another flask then distilled off the solvent under vacuum (less than 10 mbar) at 70° C.

for 12 hr. The obtained solid was dried for more 2 hr under vacuum at 70° C. to obtain 0.2 gr form T17.

Example 26: Synthesis Procedure from SLN-103 to SLN-104

In a 3 L, 3-necked, round-bottomed flask were charged 150.0 gr bis(trifluoromethyl)phenyl)-1H-1,2,4-triazole (SLN-103), Acetonitrile (1.2 lit, 8V) and charged Potassium Carbonate (110.3 gr, 1.5 eq) stirred for 30.0 min at 20-25° C. Charged 1,4-Diazabicyclo[2.2.2]octane DABCO (89.1 gr, 1.5 eq) and cooled down to −5 to 5° C. in 25 mins. To this reaction mass, added (Z)-Methyl 3-iodoacrylate solution (167.8 gr, 1.5 eq) prepared in Acetonitrile (0.3 lit, 2V) at −5 to 5° C. within 110 min. Maintained the reaction mass at −5 to 5° C. for 3 hrs, monitored by HPLC till SLN103 NMT 1.0%. Once the reaction completes, charged Water (1.5 lit 10V) at 0 to 5° C. and stirred for 1 hr at 0 to 5° C. Filtered the compound and washed with water (0.3 lit, 2V) (Yield 88%, purity 98.75%, E-isomer impurity 0.89%).

Example 27: Synthesis Procedure from SLN-104 to SLN-105

In a 3 L, 3-necked, round-bottomed flask were charged 100.0 gr (Z)-methyl 3-(3-(3,5-bis(trifluoromethyl)phenyl)-1H-1,2,4-triazol-1-yl)acrylate (SLN-104, prepared according to example 26), Tertiary Butanol (0.25 lit, 2.5V), Water (0.5 lit 5V) at 20-30° C. Charged Lithium hydroxide monohydrate (46.0 gr, 4 eq) stirred at 20-30° C. for 1 hr. The reaction mass was stirred for 1 hr and monitored by HPLC (till SLN-104 NMT 1.0%). Once the reaction completes, charge Water (0.5 lit, 5V) and additional 0.25 lit tert-butanol at 20 to 30° C. and adjusted pH to 2 using 1:1 dil HCl (0.2 lit, 2 V) stirred for 1 hr at 20-30° C. Filtered the compound and washed with water (0.2 lit, 2V). Dried the wet cake at 50-55° C., under vacuum (600 to 700 mm Hg) for 8 hrs (Yield 94%).

Example 28: Preparation of Selinexor

In a 3-L, 3-necked, round-bottomed flask were charged 60.0 gr (Z)-3-(3-(3,5-bis(trifluoromethyl)phenyl)-1H-1,2,4-triazol-1-yl)acrylic acid (SLN-105, prepared according to examples 27), Ethyl acetate (0.42 lit, 7V) and Acetonitrile (0.3 lit, 5V) at 20-25° C. Charged 2-hydrazino pyrazine (19.8 gr, 1.05 eq) then cooled to 0 to 5° C. Charged EDC.HCl (1-Ethyl-3-(3-dimethylaminopropyl) carbodiimide hydrochloride) (49.1 gr 1.5 eq) at 0 to 5° C. The reaction mass was stirred for 3 hrs and monitored by HPLC (till SLN-105 NMT 1.0%). Once the reaction completes, charge water (0.1 lit, 2V) and stirred for 15-30 min at 15-20° C., settled and separated the organic layer. Collected the organic layer and washed with sodium bicarbonate solution (0.5 lit, 5V). Finally washed the organic layer with water (0.2 lit, 2 V) and combined the collected organic layer containing the product. The solvent is distilled off under vacuum at 50 to 60° C. for 30 min. To the obtained solid, added absolute Ethanol (0.6 lit, 10V) and stirred for 30 min at 20-25° C. then cooled to 0-5° C. and stirred for 1 hr at 0-5° C. Filtered the compound under vacuum at 20-25° C. and washed with Ethanol (0.2 lit, 2V). The wet cake was dried at 55-60° C. under vacuum (600 to 700 mm Hg) for 4 hrs. (Yield 83%).

Example 29: Process for Preparation of Selinexor

Charged 50 gm (1.0 eq) (Z)-3-((3,5-bis(trifluoromethyl) phenyl)-1H-1,2,4-triazol-1-yl)acrylic acid (described here as SLN-105, prepared according to example 27) in 0.5 L of methanol at 20-30° C. Charged 2-hydrazino Pyrazine (17.25 gm, 1.10 eq.) at 20-30° C. and cooled the reaction mass to 0-5° C. Charged 42.24 gm (1.5 eq) of EDC.HCl (1-Ethyl-3-(3-dimethylaminopropyl) carbodiimide hydrochloride) at 0-5° C. The reaction was stirred for 2 hr and the reaction completion was confirmed by HPLC. After completion of reaction 1.0 L water was charged to the reactor maintaining the reaction mass temperature between 0-5° C. Stirred the slurry for 1 hr at 0-5° C. Filtered the slurry and washed the wet cake with 0.25 L water. The wet cake was semidried under vacuum at 30° C. till moisture content is between 5-10% to get Selinexor (Yield: 57.6 gm).

Example 30: Process for Preparing Selinexor

Charged 50 gm (1.0 eq) (Z)-3-((3,5-bis(trifluoromethyl) phenyl)-1H-1,2,4-triazol-1-yl)acrylic acid (described here as SLN-105, prepared in example 27) in 0.25 L of methanol at 20-30° C. Charged 2-hydrazino Pyrazine (17.25 gm, 1.10 eq.) at 20-30° C. and cooled the reaction mass to 0-5° C. Charged 42.24 gm (1.5 eq) of EDC.HCl (1-Ethyl-3-(3-dimethylaminopropyl) carbodiimide hydrochloride) at 0-5° C. The reaction was stirred for 2 hr and the reaction completion was confirmed by HPLC. Further cooled the reaction mass to −5-0° C. Stirred the slurry for 1 hr at −5-0° C. Filtered the slurry and washed the wet cake with 0.10 L chilled methanol. According to XRD measurement Selinexor form T8 was obtained (Yield: 91% on dried basis, 63 gm (wet)) (typical water content of wet Selinexor is in the range of 3.9-6 wt %).

Example 31: Process for Preparation of Pure Selinexor

Charged 57.6 gm of Selinexor (obtained from Example 29 or Example 30) and 403 ml methanol to the reactor. Heated the mass to 55-60° C. to get clear solution. Charged charcoal 8.64 gm and stirred for 30 min, filtered through hyflow bed and washed the bed with 58 ml methanol. Filtrate heated to 50° C. and stirred for 15 min at 50° C., Slowly cooled the filtrate to 20-25° C. over a period of 1 hr under nitrogen. Crystallization observed, stirred the slurry for 30 min at 20-25° C. under nitrogen. Cooled the slurry to 0-5° C. over a period of 1 hr under nitrogen. Stirred for 1 hr. at 0-5° C. under nitrogen. Filtered the slurry and washed the wet cake with 0.2 liter chilled (0-5° C.) methanol under nitrogen. Dried under vacuum (in VTD) at 50-55° C. According to XRD measurement form T8 was obtained (Yield: 46.9 gm, Purity: 99.88%).

Example 32: Process for Preparation of Pure Selinexor

Charged 63 gm wet Selinexor (obtained e.g. from example 29 or example 30) and 175 ml methanol to the reactor. Heated the mass to 55° C. to get clear solution. Charged charcoal 7.5 gm and stirred for 30 min, filtered through hyflow bed and washed the bed with 25 ml methanol. Filtrate heated to 50° C. and stirred for 15 min at 50° C.—Cooled the filtrate to 30-35° C. under nitrogen. Crystallization observed, stirred the slurry for 30 min at 25-30° C. under nitrogen. Cooled the slurry to 0-5° C. over a period of 30 min under nitrogen. Stirred for 1 hr. at 0-5° C. under nitrogen. Filtered the slurry and washed the wet cake with 0.2 liter chilled (0-5° C.) methanol under nitrogen. Dried under vacuum (in VTD) at 50-55° C. According to XRD measurement form T8 was obtained (Yield: 39 gm, Purity: 99.93%).

Example 33: Synthesis Procedure for Preparation of SLN-103

3, 5-bis (trifluoromethyl) benzamide is used as a starting material in this synthesis. This staring material can be produced by the following procedures a and b.

Procedure a. Charged 3,5-bis(trifluoromethyl)benzonitrile (100 gm, 1 meq.), Potassium carbonate (63.5 gm, 1.1 meq.) into 600 ml Dimethyl sulphoxide and cooled the reaction mass to 15-20° C. Added 30% $H_2O_2$ solution (100 gm, 2.1 eq and stirred for 2-3 hrs. at 20-30° C. and reaction completion confirmed by HPLC. Reaction mass quenched by addition of water (3 L, 30 vol). Filtered the slurry and washed the wet cake by water (500 ml, 5 vol)). Dried under vacuum at 50-60° C. to get 105 gm 3, 5-bis (trifluoromethyl) benzamide (Purity: ~99%).

Procedure b. Charged 3,5-bis(trifluoromethyl)benzonitrile (100 gm, 1 meq.), 2 (N) Sodium hydroxide (21.7 gm, 1.3 meq.) into 400 ml methanol and stirred the reaction mass at 20-30° C. for 2-3 hrs. Added Dimethyl sulphoxide (100 ml) followed by dilute 30% $H_2O_2$ solution (100 gm diluted in 300 ml water, 2.1 eq.) at 20-35° C. Stirred the mass for 2-3 hrs. at 20-30° C. and confirmed reaction completion by HPLC. Reaction mass quenched by addition of water (500 ml, 5 Vol). Filtered the slurry and washed the wet cake by water (500 ml, 5 Vol). Dried under vacuum at 50-60° C. to get 100 gm 3, 5-bis (trifluoromethyl) benzamide (Purity~99%). Charged 3, 5-bis (trifluoromethyl) benzamide, prepared according to procedures a or b, as described above, (100 gm, 1 meq) into N, N Dimethyl formamide (100 ml, 1 vol). Added N, N Dimethyl formamide dimethyl acetal (70 gm, 1.5 meq) at 20-30° C. and stirred the reaction mass for 2-3 hrs. Reaction completion for the formation N-((dimethylamino)methylene)-3,5-bis(trifluoromethyl)benzamide was confirmed by HPLC. Cooled reaction mass to 10-15° C. and added acetic acid (500 ml, 5 vol.) followed by hydrazine hydrate (31 gm, 1.5 meq). Reaction mass was heated to 50-55° C. and stirred for 2-3 hrs. at same temperature. Reaction was monitored by HPLC. Cooled reaction mass to 20-30° C. and quenched by addition of water (2.5 L, 25 vol.). Filtered the slurry and washed the wet cake by water (500 ml, 5 vol.). Dried under vacuum at 50-60° C. to get 3-(3,5-bis(trifluoromethyl)phenyl)-1H-1,2,4-triazole (94 gr, Purity~97%).

The invention claimed is:

1. A crystalline form of Selinexor designated as Form T8, characterized by data selected from one or more of the following:
    a. an X-ray powder diffraction pattern having peaks at 6.0, 13.4, 17.6, 19.6, and 24.9 degrees 2-theta±0.2 degrees 2-theta;
    b. an XRPD pattern as depicted in FIG. 8;
    c. a solid state $^{13}$C-NMR spectrum having characteristic peaks at 107.5, 126.0, 132.2, 141.5, 151.7 and 157.9 ppm±0.2 ppm;
    d. a solid state $^{13}$C-NMR spectrum having the following chemical shift absolute differences from a reference peak at 154.1 ppm±2 ppm of 46.6, 28.1, 21.9, 12.6, 2.4 and 3.8 ppm±0.1 ppm;
    e. a solid state $^{13}$C-NMR spectrum as depicted in FIG. 18 or 19 or 20; and
    f. a combination of any two or more of the above.

2. The crystalline Form T8 of Selinexor according to claim 1, characterized by an XRPD pattern having peaks at 6.0, 13.4, 17.6, 19.6, and 24.9 degrees 2-theta±0.2 degrees 2-theta, and also having one, two, three, four or five additional peaks selected from 15.3, 20.8, 23.3, 26.4 and 29.6 degrees two theta±0.2 degrees two theta.

3. A crystalline form of Selinexor designated as Form T1, characterized by data selected from one or more of the following:
    a. an XRPD pattern having peaks 10.2, 16.9, 21.1, 21.5, 22.7, and 26.7 degrees 2-theta±0.2 degrees 2-theta;
    b. an XRPD pattern as depicted in FIG. 1; and
    c. a combination of (a) and (b).

4. The crystalline Form T1 of Selinexor according to claim 3, characterized by an XRPD pattern having peaks at 10.2, 16.9, 21.1, 21.5, 22.7, and 26.7 degrees 2-theta±0.2 degrees 2-theta, and also having one, two, three, four or five additional peaks selected from 5.8, 19.2, 19.7, 23.5 and 24.3 degrees two theta±0.2 degrees two theta.

5. A crystalline form of Selinexor designated as Form T6, characterized by data selected from one or more of the following:
    a. an XRPD pattern having peaks at 13.0, 13.7, 20.1, 23.2, 23.9 and 27.7 degrees 2-theta±0.2 degrees 2-theta;
    b. an XRPD pattern as depicted in FIG. 6; and
    c. a combination of (a) and (b).

6. The crystalline Form T6 of Selinexor according to claim 5, characterized by an XRPD pattern having peaks at 13.0, 13.7, 20.1, 23.2, 23.9 and 27.7 degrees 2-theta±0.2 degrees 2-theta, and also having one, two, three, four or five additional peaks selected from 5.4, 10.9, 21.2, 26.2 and 27.1 degrees two theta±0.2 degrees two theta.

7. A crystalline form of Selinexor designated as Form T7, characterized by data selected from one or more of the following:
    a. an XRPD pattern having peaks 15.1, 15.5, 21.6, 24.0 and 26.4 degrees 2-theta±0.2 degrees 2-theta;
    b. an XRPD pattern as depicted in FIG. 7; and
    c. a combination of (a) and (b).

8. The crystalline Form T7 of Selinexor according to claim 7, characterized by an XRPD pattern having peaks at 15.1, 15.5, 21.6, 24.0 and 26.4 degrees 2-theta±0.2 degrees 2-theta, and also having one, two, three, four or five additional peaks selected from 16.2, 18.3, 23.3, 30.4 and 34.3 degrees two theta±0.2 degrees two theta.

9. A pharmaceutical composition comprising a crystalline form according to claim 1, optionally further comprising at least one pharmaceutically acceptable excipient.

10. A process for preparing the pharmaceutical formulation according to claim 9, comprising combining the crystalline form with at least one pharmaceutically acceptable excipient.

11. A method of treating a cancer that is treatable by the selective inhibition of nuclear export, comprising administering a therapeutically effective amount of the crystalline form according to claim 1 to a subject suffering from cancer, otherwise in need of the treatment.

12. A pharmaceutical composition comprising a crystalline form according to claim 3, optionally further comprising at least one pharmaceutically acceptable excipient.

13. A pharmaceutical composition comprising a crystalline form according to claim 5, optionally further comprising at least one pharmaceutically acceptable excipient.

14. A pharmaceutical composition comprising a crystalline form according to claim 7, optionally further comprising at least one pharmaceutically acceptable excipient.

15. A process for preparing the pharmaceutical formulation according to claim 12, comprising combining the crystalline form with at least one pharmaceutically acceptable excipient.

16. A process for preparing the pharmaceutical formulation according to claim 13, comprising combining the crystalline form with at least one pharmaceutically acceptable excipient.

17. A process for preparing the pharmaceutical formulation according to claim 14, comprising combining the crystalline form with at least one pharmaceutically acceptable excipient.

18. A method of treating a cancer that is treatable by the selective inhibition of nuclear export, comprising administering a therapeutically effective amount of the crystalline form according to claim 3 to a subject suffering from cancer, otherwise in need of the treatment.

19. A method of treating a cancer that is treatable by the selective inhibition of nuclear export, comprising administering a therapeutically effective amount of the crystalline form according to claim 5 to a subject suffering from cancer, otherwise in need of the treatment.

20. A method of treating a cancer that is treatable by the selective inhibition of nuclear export, comprising administering a therapeutically effective amount of the crystalline form according to claim 7 to a subject suffering from cancer, otherwise in need of the treatment.

\* \* \* \* \*